(12) United States Patent
Abboud et al.

(10) Patent No.: US 8,608,730 B2
(45) Date of Patent: Dec. 17, 2013

(54) CRYOABLATION CATHETER HANDLE

(75) Inventors: Marwan Abboud, Pierrefonds (CA); Domenic Santoianni, Kirkland (CA); Philippe Marchand, Lake Forest, CA (US); Rachid Mahrouche, Lasalle (CA); Patrick St-Louis, Boisbriand (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 1735 days.

(21) Appl. No.: 11/220,268

(22) Filed: Sep. 6, 2005

(65) Prior Publication Data

US 2006/0047273 A1   Mar. 2, 2006

Related U.S. Application Data

(63) Continuation-in-part of application No. 10/256,756, filed on Sep. 27, 2002, now abandoned, which is a continuation-in-part of application No. 10/202,991, filed on Jul. 25, 2002, now Pat. No. 6,746,445, which is a continuation of application No. 09/556,042, filed on Apr. 21, 2000, now Pat. No. 6,440,126.

(60) Provisional application No. 60/130,538, filed on Apr. 21, 1999.

(51) Int. Cl.
   *A61B 18/18* (2006.01)
(52) U.S. Cl.
   USPC .............................................. 606/21; 606/22
(58) Field of Classification Search
   USPC ...................................... 606/20–52; 604/523
   See application file for complete search history.

(56) References Cited

U.S. PATENT DOCUMENTS

| | | | | |
|---|---|---|---|---|
| 3,980,112 A | * | 9/1976 | Basham | 141/392 |
| 4,043,341 A | | 8/1977 | Tromovitch | |
| 4,534,339 A | | 8/1985 | Collins et al. | |
| 4,617,012 A | * | 10/1986 | Vaillancourt | 604/29 |
| 4,919,112 A | | 4/1990 | Siegmund | |
| 4,946,440 A | * | 8/1990 | Hall | 604/164.09 |
| 5,078,713 A | | 1/1992 | Varney | |
| 5,098,428 A | | 3/1992 | Sandlin et al. | |
| 5,170,787 A | | 12/1992 | Lindegren | |
| 5,217,482 A | | 6/1993 | Keith | |
| 5,239,982 A | * | 8/1993 | Trauthen | 600/117 |
| 5,281,213 A | | 1/1994 | Milder et al. | |
| 5,324,286 A | | 6/1994 | Fowle | |
| 5,334,181 A | | 8/1994 | Rubinsky et al. | |

(Continued)

*Primary Examiner* — Linda Dvorak
*Assistant Examiner* — Amanda Scott
(74) *Attorney, Agent, or Firm* — Christopher & Weisberg, P.A.

(57) ABSTRACT

A thermal treatment medical system including an umbilical having a first portion and a second portion, and a connector including a male coupling body connected to the first portion, the male coupling body having a central shank defining first and second lumens, a female coupling body connected to the second portion, the female coupling body, matable with the male coupling body and defining third and fourth lumens matable to be in fluid communication with the first and second lumens, respectively, to define first and second fluid flow pathways, respectively, through the connector when the male coupling body is mated with the female coupling body. The second fluid flow pathway is co-axially disposed about a central axis coincident with the first fluid flow pathway. The connector includes a mating mechanism for spatially locking the male and female coupling bodies with respect to each other. Additionally, the thermal treatment medical system includes a multiple lumen co-axial connector for connecting the catheter flow pathways with a fluid source and control console.

4 Claims, 18 Drawing Sheets

(56) References Cited

U.S. PATENT DOCUMENTS

| | | | | |
|---|---|---|---|---|
| 5,344,398 | A | 9/1994 | Hara | |
| 5,395,348 | A * | 3/1995 | Ryan | 604/247 |
| 5,423,807 | A | 6/1995 | Milder | |
| 5,452,582 | A | 9/1995 | Longsworth | |
| 5,466,020 | A * | 11/1995 | Page et al. | 285/361 |
| 5,605,539 | A * | 2/1997 | Buelna et al. | 604/508 |
| 5,658,278 | A | 8/1997 | Imran et al. | |
| 5,674,218 | A | 10/1997 | Rubinsky et al. | |
| 5,685,878 | A | 11/1997 | Falwell et al. | |
| 5,697,927 | A | 12/1997 | Imran et al. | |
| 5,715,817 | A | 2/1998 | Stevens-Wright et al. | |
| 5,733,319 | A | 3/1998 | Neilson et al. | |
| 5,755,663 | A | 5/1998 | Larsen et al. | |
| 5,846,235 | A * | 12/1998 | Pasricha et al. | 606/23 |
| 5,860,953 | A | 1/1999 | Snoke et al. | |
| 5,860,970 | A | 1/1999 | Goddard et al. | |
| 5,910,104 | A | 6/1999 | Dobak, III et al. | |
| 5,916,212 | A | 6/1999 | Baust et al. | |
| 5,992,158 | A | 11/1999 | Goddard et al. | |
| 6,007,571 | A | 12/1999 | Neilson et al. | |
| 6,193,644 | B1 * | 2/2001 | Dobak et al. | 600/23 |
| 6,221,070 | B1 | 4/2001 | Tu et al. | |
| 6,224,624 | B1 | 5/2001 | Lasheras et al. | |
| 6,283,959 | B1 | 9/2001 | Lalonde et al. | |
| 6,383,180 | B1 | 5/2002 | Lalonde et al. | |
| 6,440,126 | B1 | 8/2002 | Abboud et al. | |
| 6,468,269 | B1 | 10/2002 | Korpan et al. | |
| 6,471,694 | B1 | 10/2002 | Kudaravalli et al. | |
| 6,746,445 | B2 * | 6/2004 | Abboud et al. | 606/22 |
| 2002/0095133 | A1 * | 7/2002 | Gillis et al. | 604/502 |
| 2003/0028182 | A1 | 2/2003 | Abboud et al. | |

* cited by examiner

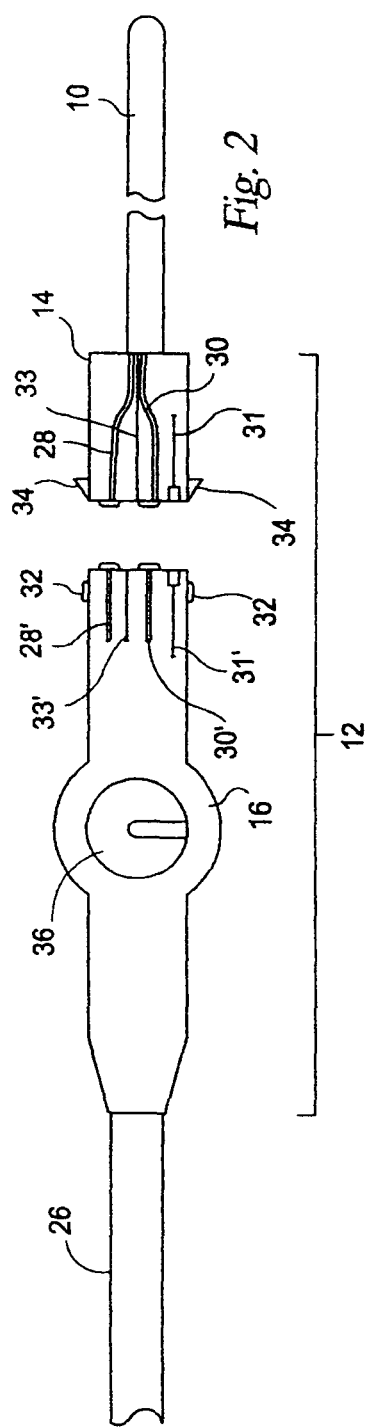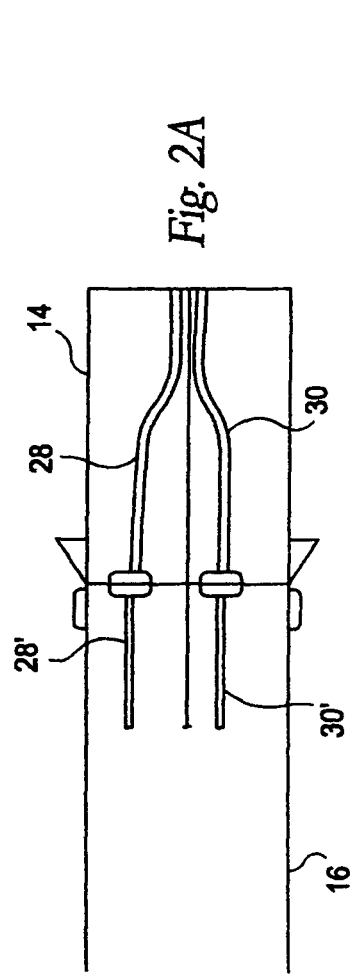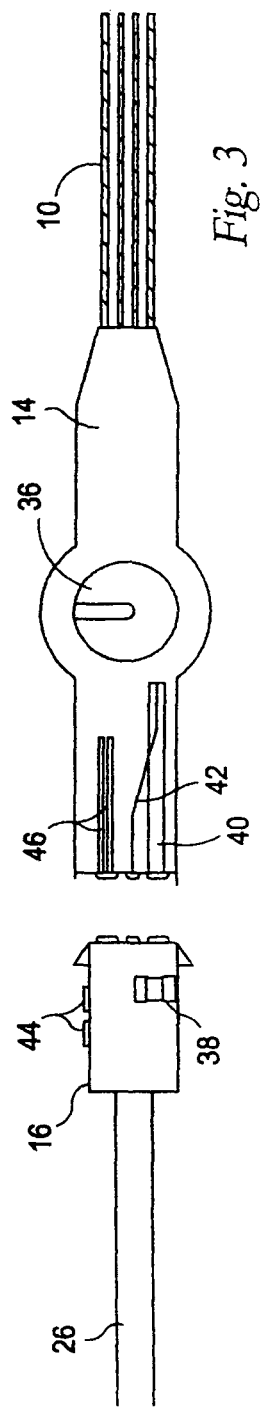

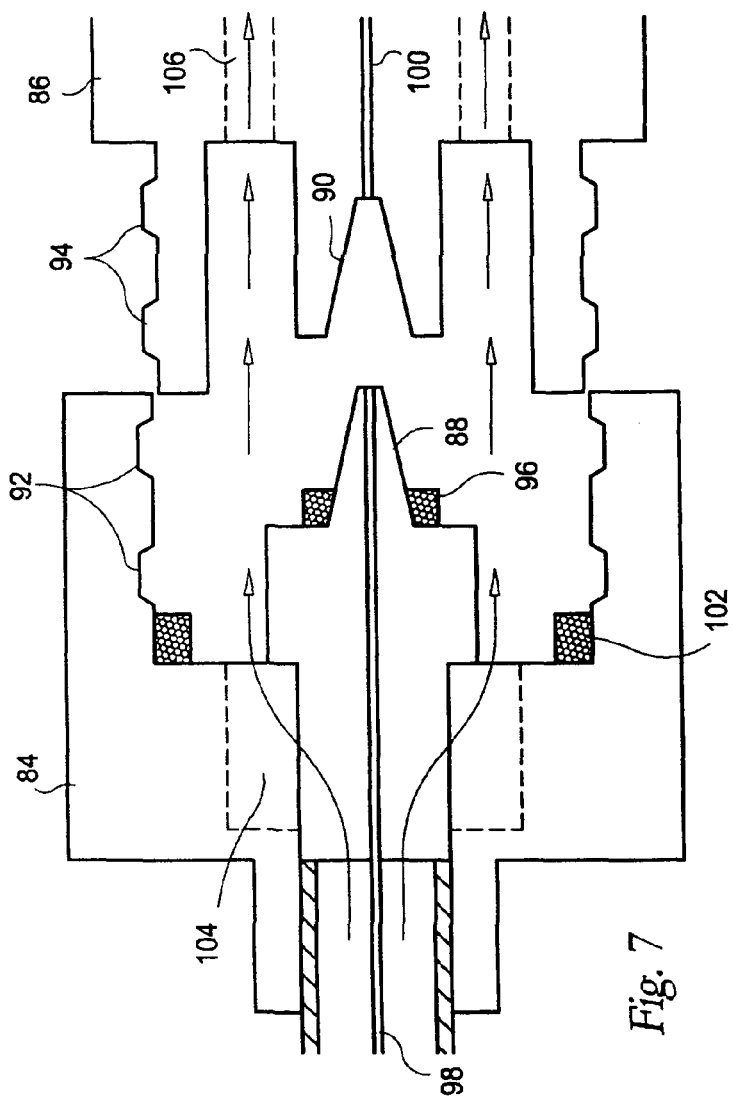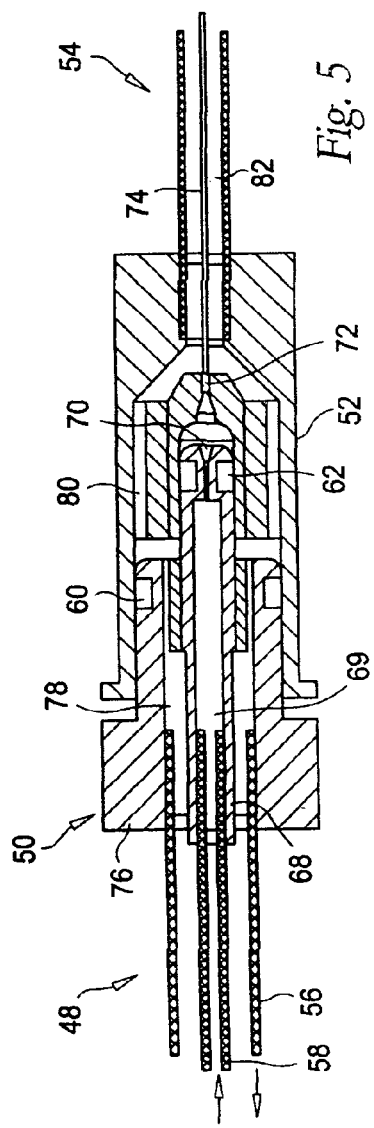

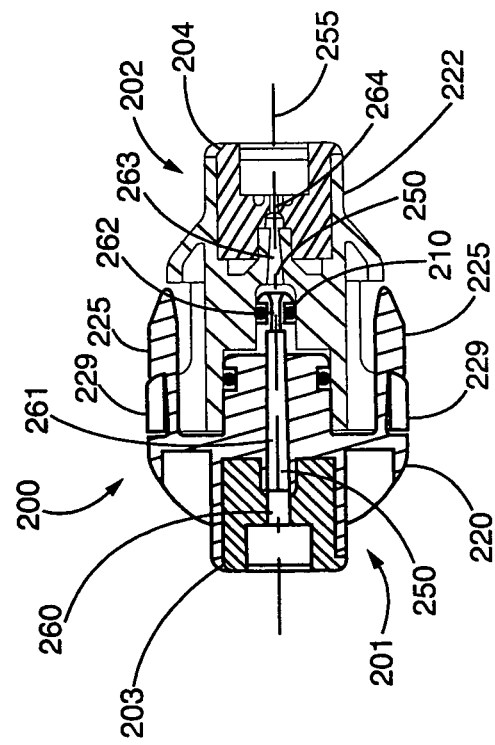
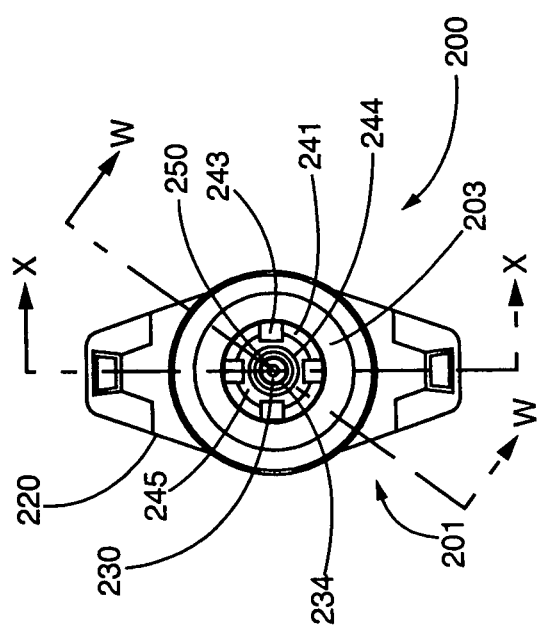

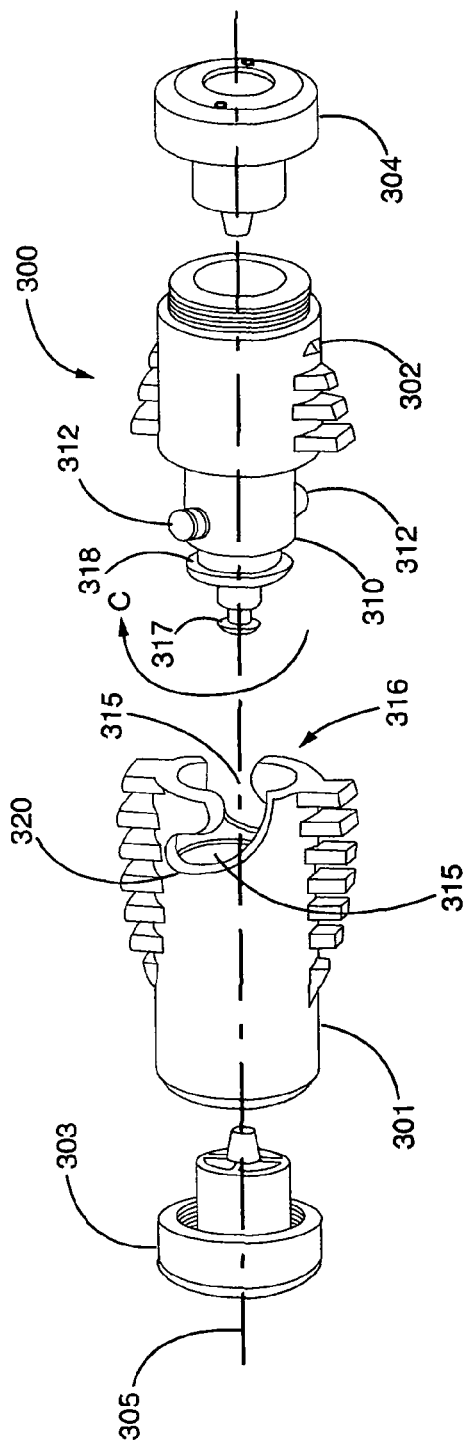
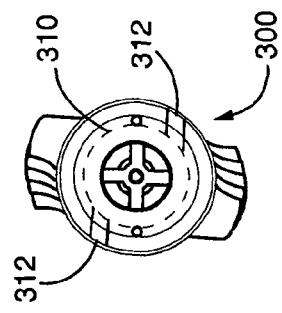
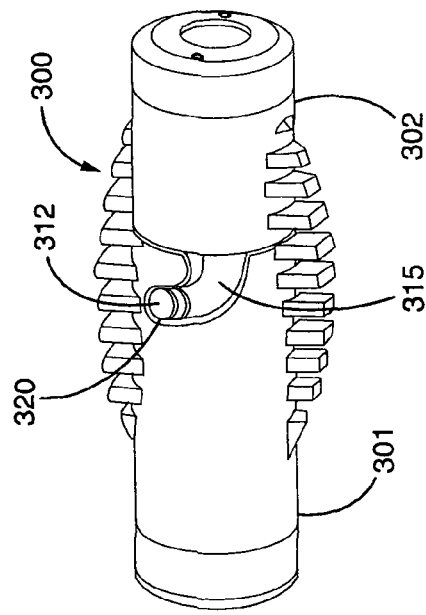

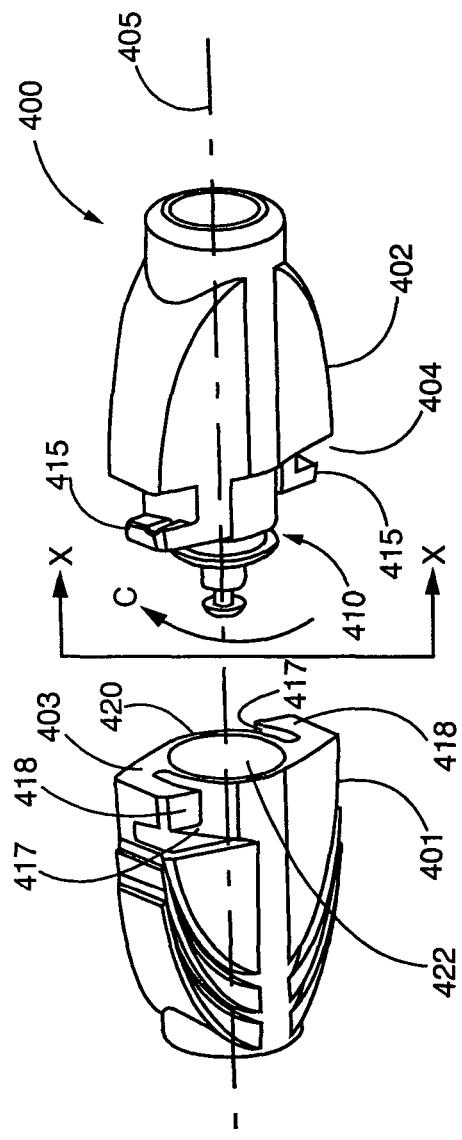
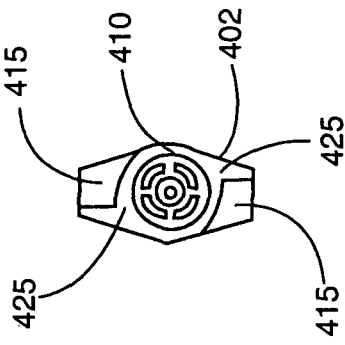
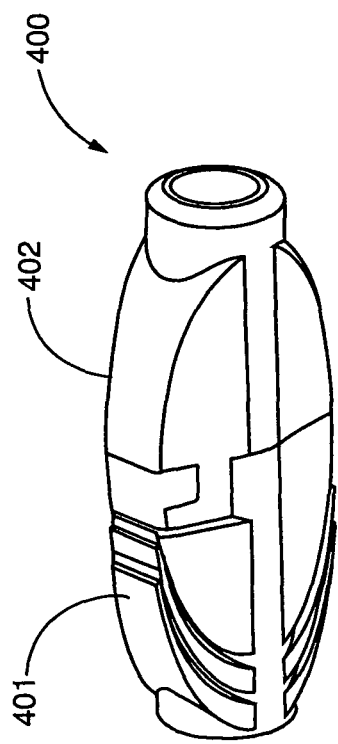
FIG 11A
FIG 11C
FIG 11B

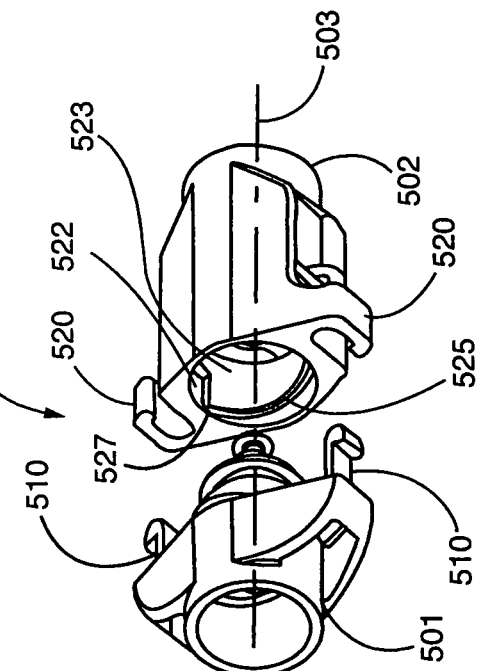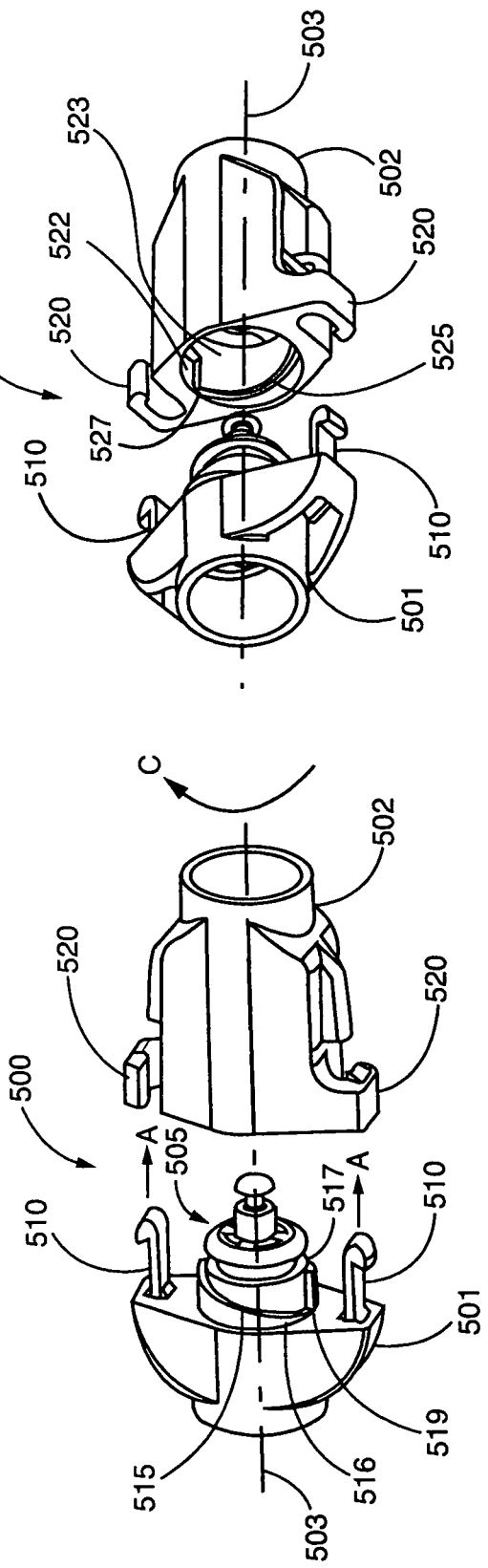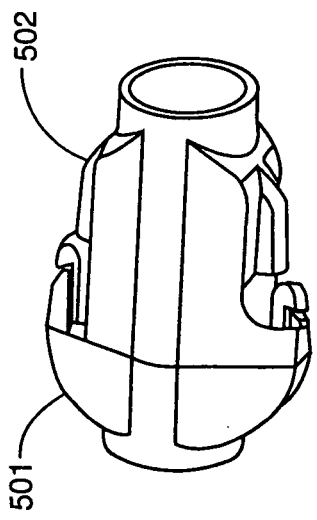

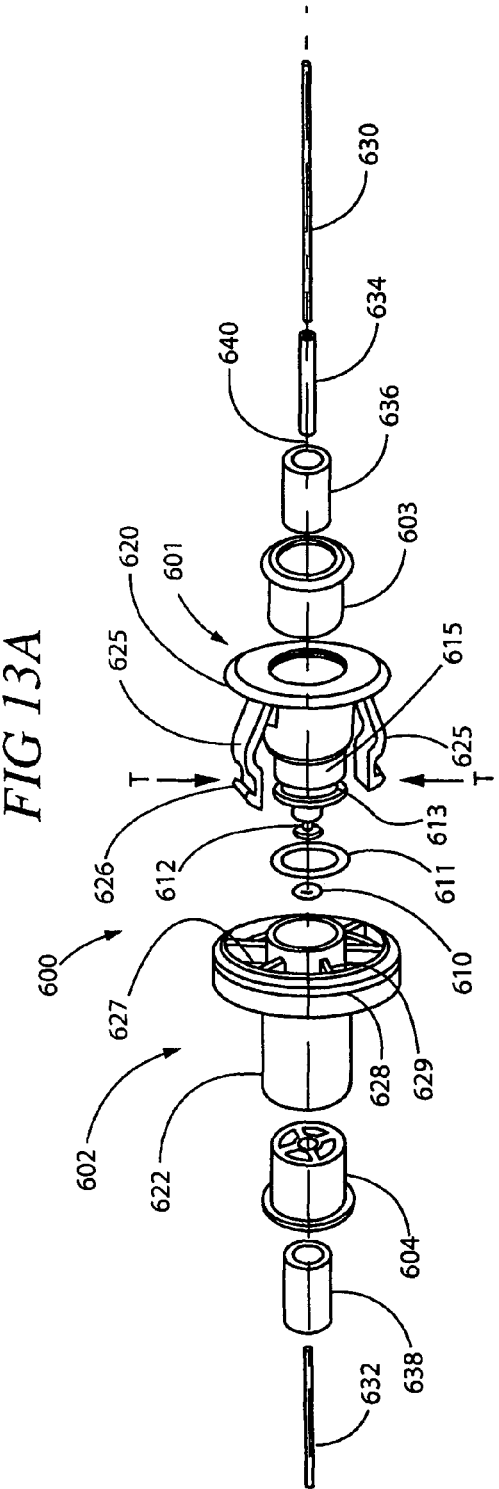
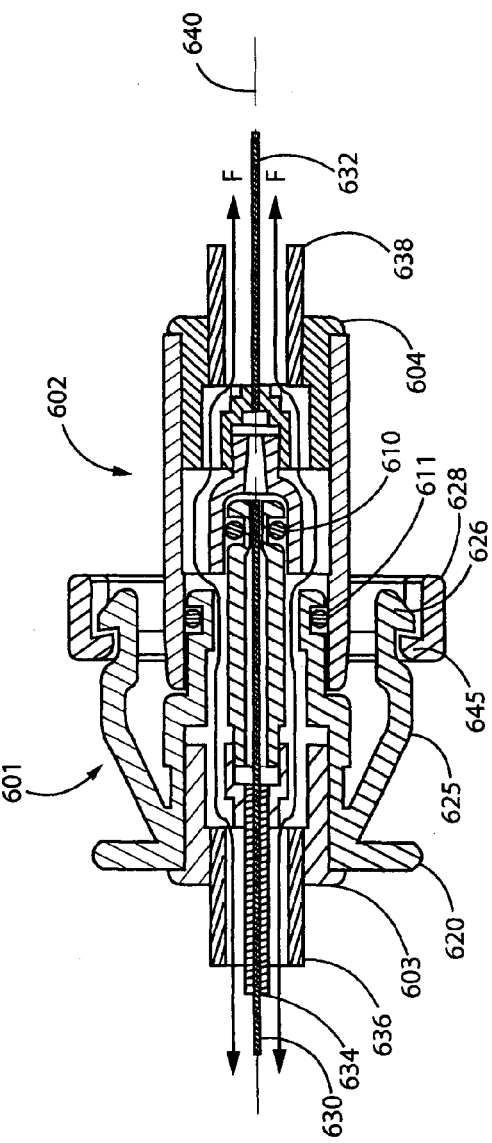

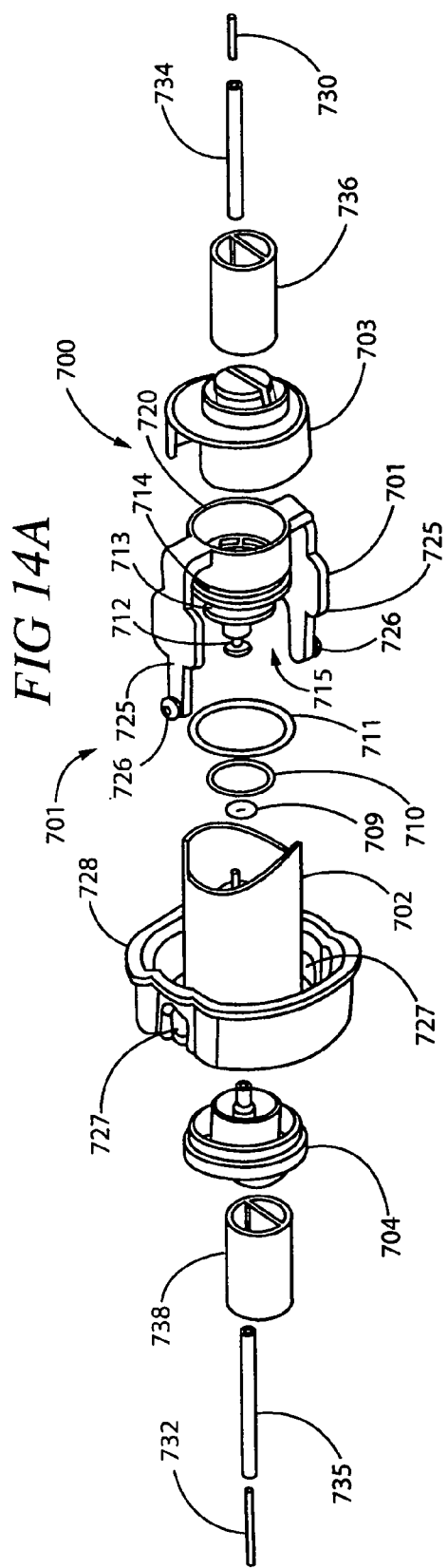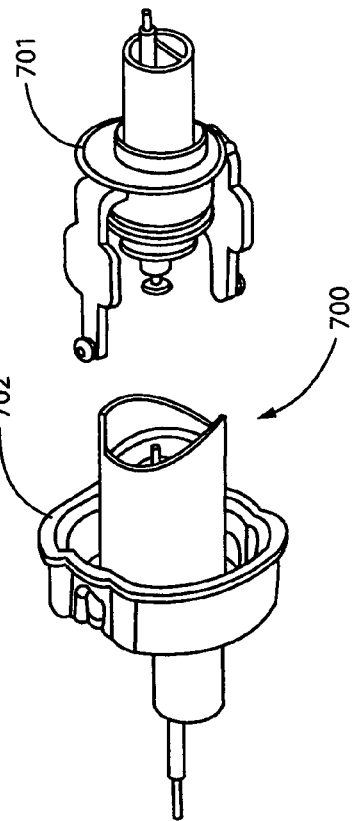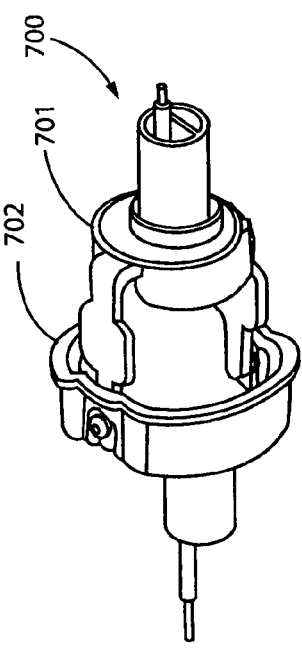

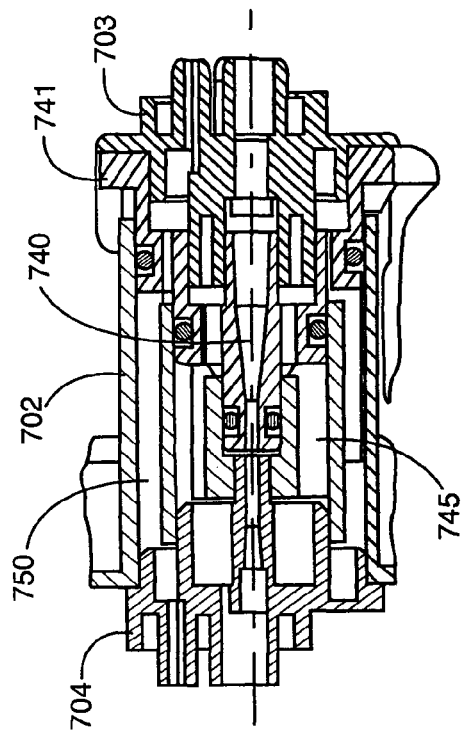
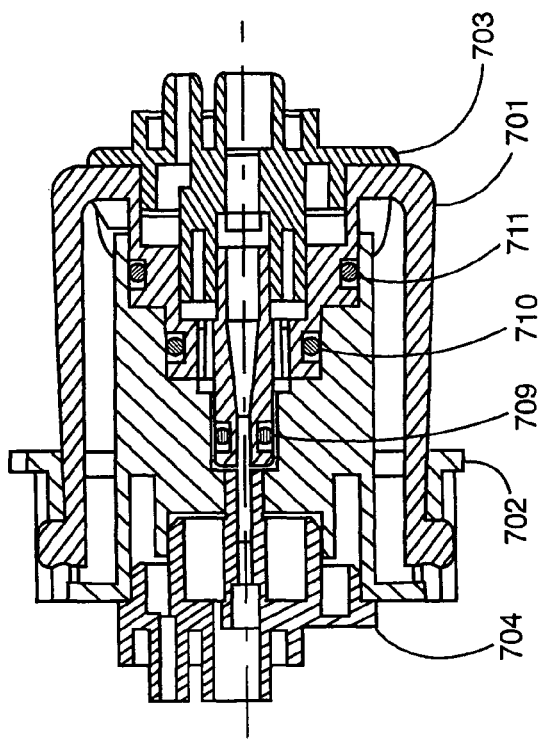
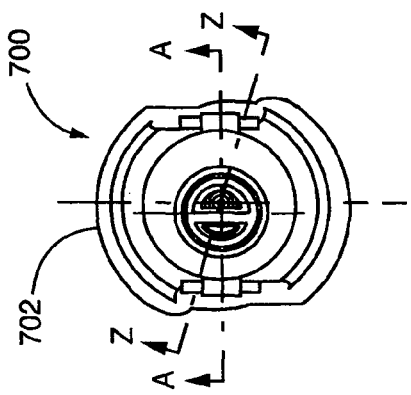

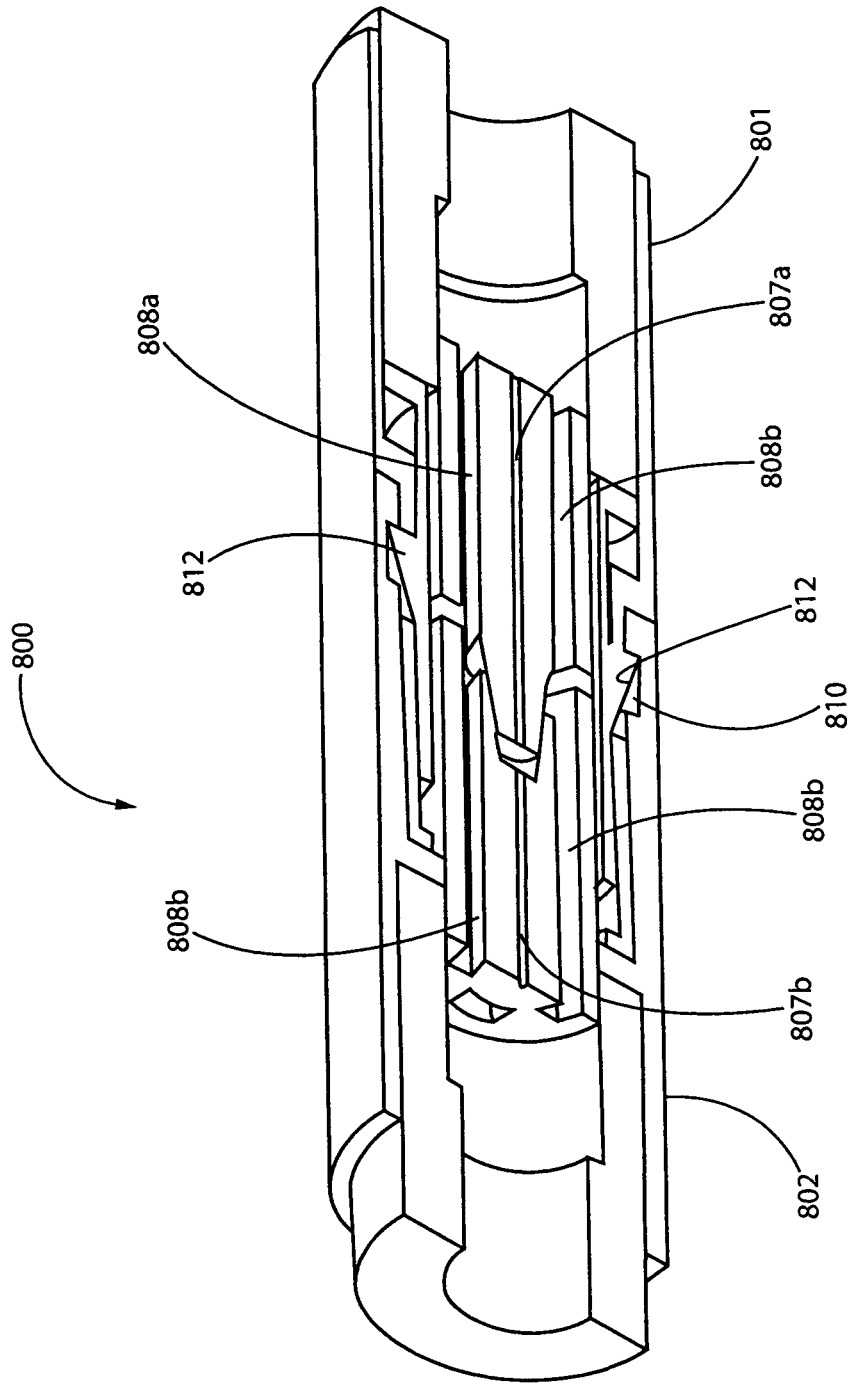

CRYOABLATION CATHETER HANDLE

CROSS-REFERENCE TO RELATED APPLICATION

This application is a continuation-in-part of pending U.S. application Ser. No. 10/256,756 filed Sep. 27, 2002 by Marwan Abboud, et al., entitled CRYOABLATION CATHETER HANDLE, which is a continuation-in-part of U.S. patent application Ser. No. 10/202,991, filed Jul. 25, 2002, entitled CRYOABLATION CATHETER HANDLE, now issued U.S. Pat. No. 6,746,445, which is a continuation of allowed application Ser. No. 09/556,042, filed Apr. 21, 2000, by Marwan Abboud, et al., entitled CRYOABLATION CATHETER HANDLE, now issued U.S. Pat. No. 6,440,126, which claims priority from U.S. Patent Application Ser. No. 60/130,538, filed Apr. 21, 1999, all of which are incorporated herein by reference.

STATEMENT REGARDING FEDERALLY SPONSORED RESEARCH OR DEVELOPMENT n/a

FIELD OF THE INVENTION

This invention relates to medical systems, and more particularly to handles and connectors for cryogenic medical systems and catheters.

BACKGROUND OF THE INVENTION

A cryogenic catheter can generally be described as an elongate, slender, flexible body that is capable of delivering extreme cold to provide a medically therapeutic effect. Such a catheter can be a part of a system that includes several components, such as a console, an umbilical, connectors, a cryoablation catheter and a handle.

The console houses the electronics and software for controlling an ablation procedure. Additionally, the console controls delivery of a refrigerant through the umbilical to the catheter, and controls recovery of the refrigerant from the catheter.

The umbilical connecting the catheter and/or handle to the console provides mechanical connections for refrigerant transport and electrical connection for electrical devices and sensors. The handle, in addition to providing an appropriate graspable structure, can include controls for catheter steering, as well as other catheter functions. Various connectors can be connected to the umbilical to provide the connections to the thermal treatment system.

Known cryogenic catheter systems provide a unitary handle and catheter which is intended for a single use. As with other devices, attention to the percentage and content of a system that is disposable (or that which must be disposed of for sanitary reasons), as well as attention to the cost of replacement items, can have a substantial effect on the cost of acquisition and operation of the system. Thus, if possible, it would help to reduce cost of the system if only the catheter (or a portion thereof) was disposable and, under most circumstances, the handle was available for reuse.

Ideally, the inclusion of disposable system elements does not compromise system performance or patient safety. However, known attempts to provide disposable catheter elements have been less than ideal. For example, providing a catheter that is removable from the handle requires not only connection to refrigerant, steering elements and electrical elements, but also a creation of a fluid-tight seal at the catheter/handle interface. Not only can it be tedious to make such connections, known devices or connectors with this type of feature have not proved to be acceptable with respect to either performance or safety.

It would therefore be desirable to provide a cryogenic catheter that provides the benefits of a disposable component and which is easy to use, without safety or performance limitations. Furthermore, it would be desirable to provide a connector suited for use with cryogenic catheters which would allow for the quick, efficient, and secure connection of catheter components, such as injection tubes, containment sleeves, electrical connections, sensors, and the like. Additionally, it would be desirable to provide connectors, which may be configured at various junctions of the catheter assembly so as to allow for detachable and disposable cryoablation catheter systems.

SUMMARY OF THE INVENTION

A thermal treatment medical system including an umbilical having a first portion and a second portion, and a connector including a male coupling body connected to the first portion, the male coupling body having a central shank defining first and second lumens, a female coupling body connected to the second portion, the female coupling body, matable with the male coupling body and defining third and fourth lumens matable to be in fluid communication with the first and second lumens, respectively, to define first and second fluid flow pathways, respectively, through the connector when the male coupling body is mated with the female coupling body. The second fluid flow pathway is co-axially disposed about a central axis coincident with the first fluid flow pathway. The connector includes a mating mechanism for spatially locking the male and female coupling bodies with respect to each other.

Furthermore, A thermal treatment medical system is provided, including, an umbilical having a first portion and a second portion; and a first coupling member connected to the first portion, the first coupling member having a first central longitudinal axis, a second coupling member having a second central longitudinal axis coincident with the first central longitudinal axis, and a means for coupling the first and second coupling members. The second coupling member connected to the second portion, the first coupling member is insertable into the first coupling member to define first and second fluid flow pathways. The first fluid flow pathway is coincident with the first central longitudinal axis. The second fluid flow pathway is co-axially disposed around the first fluid flow pathway and first central longitudinal axis.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 2 illustrates an exemplary embodiment of a handle as shown in FIG. 1, wherein the two handle portions are not mated;

FIG. 2A depicts the first and second handle portions of FIG. 2 in a mated state;

FIG. 3 shows an alternative embodiment of a two-part handle;

FIG. 5 is a sectional view of the two-part co-axial connector of FIG. 4 in a partially mated state;

FIG. 7 is a sectional view of another embodiment of a co-axial connector;

FIG. 9B is a side view of the connector of FIG. 9A is assembled form;

FIG. 9C is a sectional view of the connector of FIG. 9B taken along section X-X in FIG. 9B, without the injection and co-axial tubing inserted therein;

FIG. 10A is an exploded perspective view of yet another embodiment of a co-axial connector;

FIG. 10B is a perspective view of the connector of FIG. 10A in assembled form;

FIG. 10C is a side view of the connector of FIG. 10A is assembled form;

FIG. 11A is an exploded perspective view of yet another embodiment of a co-axial connector;

FIG. 11B is a perspective view of the connector of FIG. 11A in assembled form;

FIG. 11C is a side view of the male coupling of the connector of FIG. 11A, viewed in the direction X-X of FIG. 11A;

FIG. 12A is a first exploded perspective view of yet another embodiment of a co-axial connector;

FIG. 12B is a second exploded perspective view of the connector of FIG. 12A;

FIG. 12C is a perspective view of the connector of FIG. 12C in assembled form;

FIG. 13A is an exploded perspective view of yet another embodiment of a co-axial connector;

FIG. 13B is an enlarged sectional view of the connector of FIG. 13A;

FIG. 14A is an exploded perspective view of yet another embodiment of a co-axial connector;

FIG. 14B is a partially exploded perspective view of the connector of FIG. 14A in partially assembled form;

FIG. 14C is a perspective view of the connector of FIG. 14A in fully assembled form;

FIG. 14D is a side view of the connector of FIG. 14A in fully assembled form;

FIG. 14E is a sectional view of the connector of FIG. 14A taken along section A-A in FIG. 14D;

FIG. 14F is a sectional view of the connector of FIG. 14A taken along section Z-Z in FIG. 14D;

FIG. 15B is an enlarged cutaway, exploded perspective view of the connector of FIG. 15A in mated form.

DETAILED DESCRIPTION OF THE INVENTION

Figure 1:
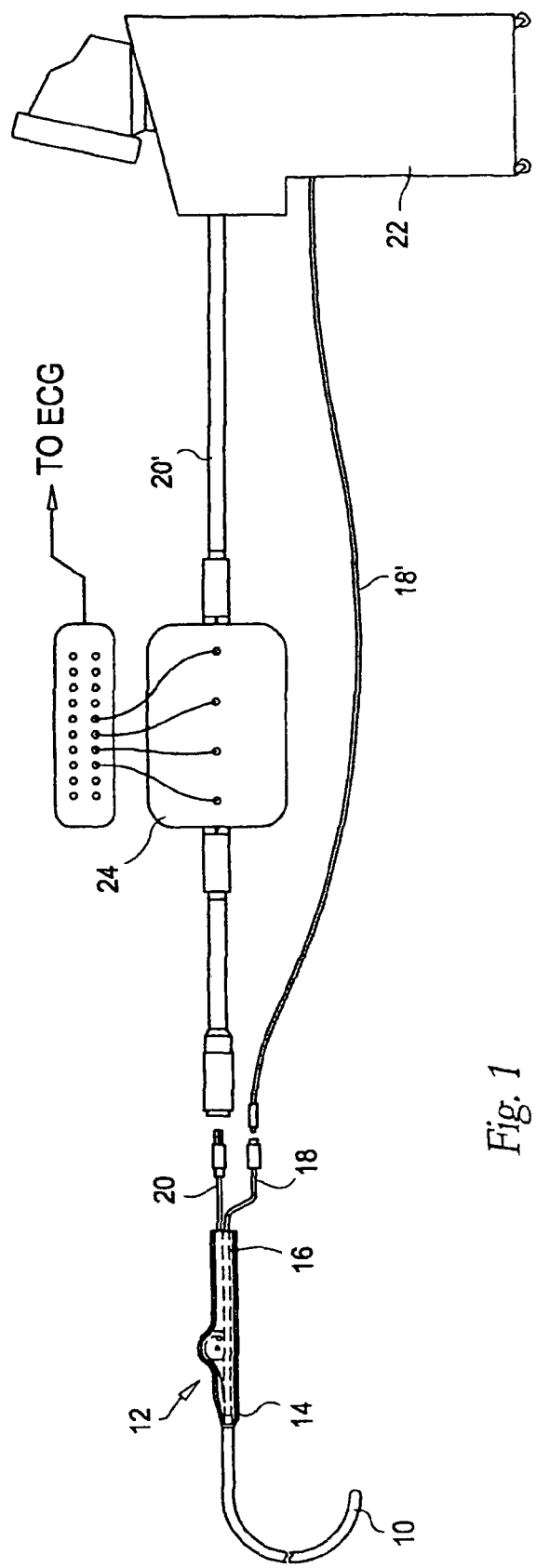
FIG. 1 illustrates a cryogenic catheter system generally.

FIG. 1 depicts a cryogenic catheter system in accordance with the invention. The system includes a catheter 10, such as those disclosed in U.S. Pat. Nos. 5,899,898 and 5,899,899 to Arless, which are incorporated herein by reference. The system also includes a handle 12 having a first portion 14 and a second portion 16. First and second umbilicals 18 and 20, respectively, connect the second portion 16 of the handle 12 to a console 22. The first umbilical 18 provides a path for a liquid or gas refrigerant to be transferred between the console 22 and the handle 12; and the second umbilical 20 provides a signal path, such as for electrical signals, between the console 22 and the handle. Additional umbilicals can be provided as required, and the functions of more than one umbilical can be provided in a single, multifunction umbilical. Further, additional devices, such as a connector box 24 can be placed in electrical communication with an umbilical. As shown in FIG. 1, the connector box 24 provides for connection to ECG apparatus (not shown). Also, one or more of the umbilicals can be divisible into two or more portions as shown in FIG. 1, wherein the first umbilical includes portion 18 and 18', and the second umbilical includes portions 20 and 20'.

Referring now to FIG. 2, additional details of an exemplary two-part handle 12 are discussed in greater detail. A first handle portion 14 is shown mated to a cryogenic catheter 10 and a second handle portion 16 is shown mated to a single, multipurpose umbilical 26. The first handle portion 14 defines or includes a portion of a first fluid pathway 28 and a portion of a second fluid pathway 30. The second handle portion 16 defines or contains a second portion of the first fluid pathway 28' and a second portion of the second fluid pathway 30'. When the first and second portions of the first and second fluid pathways are mated, as shown in FIG. 2A, continuous fluid paths are provided. Similarly, the first handle portion 14 includes a portion of one or more electrical or fiber-optic lines 31 and the second handle portion 16 includes a second portion of the one or more electrical or fiber-optic lines 31'. Further, the first handle portion 14 includes a portion of one or more steering elements, such a pull wire 33 and the second handle portion 16 includes a second portion of the steering elements 33'.

The first and second handle portions, as well as the first and second fluid pathways, one or more electrical or fiber-optic lines, and one or more steering elements are held together by complimentary locking elements 32 and 34 as is known in the art, such as locking clips, bayonet, or twist-lock. Similarly, the fluid paths are mated with couplings, the wires with electrical connectors, and the steering elements with mechanical connectors. Thus, in the exemplary embodiment, the catheter 10 can be disconnected from the umbilical 18 and discarded, while allowing the first handle portion 14, which can include steering mechanisms and other controls, to be retained for further use.

Whereas FIG. 2 shows a steering actuator, such as a thumb wheel, for selectively positioning a steering element in the second portion 16 of the handle 12, FIG. 3 shows an arrangement where the steering actuator 36 is located in the first portion 14. Additional features visible in FIG. 3 include a blood sensor 38 located and configured in such a manner so as to detect blood being withdrawn from the catheter 10 through a low pressure or vacuum exhaust line 40 along with refrigerant injected through a supply tube 42. Also shown are electrical controls 44 in communication with electrical wires 46.

Figure 4:
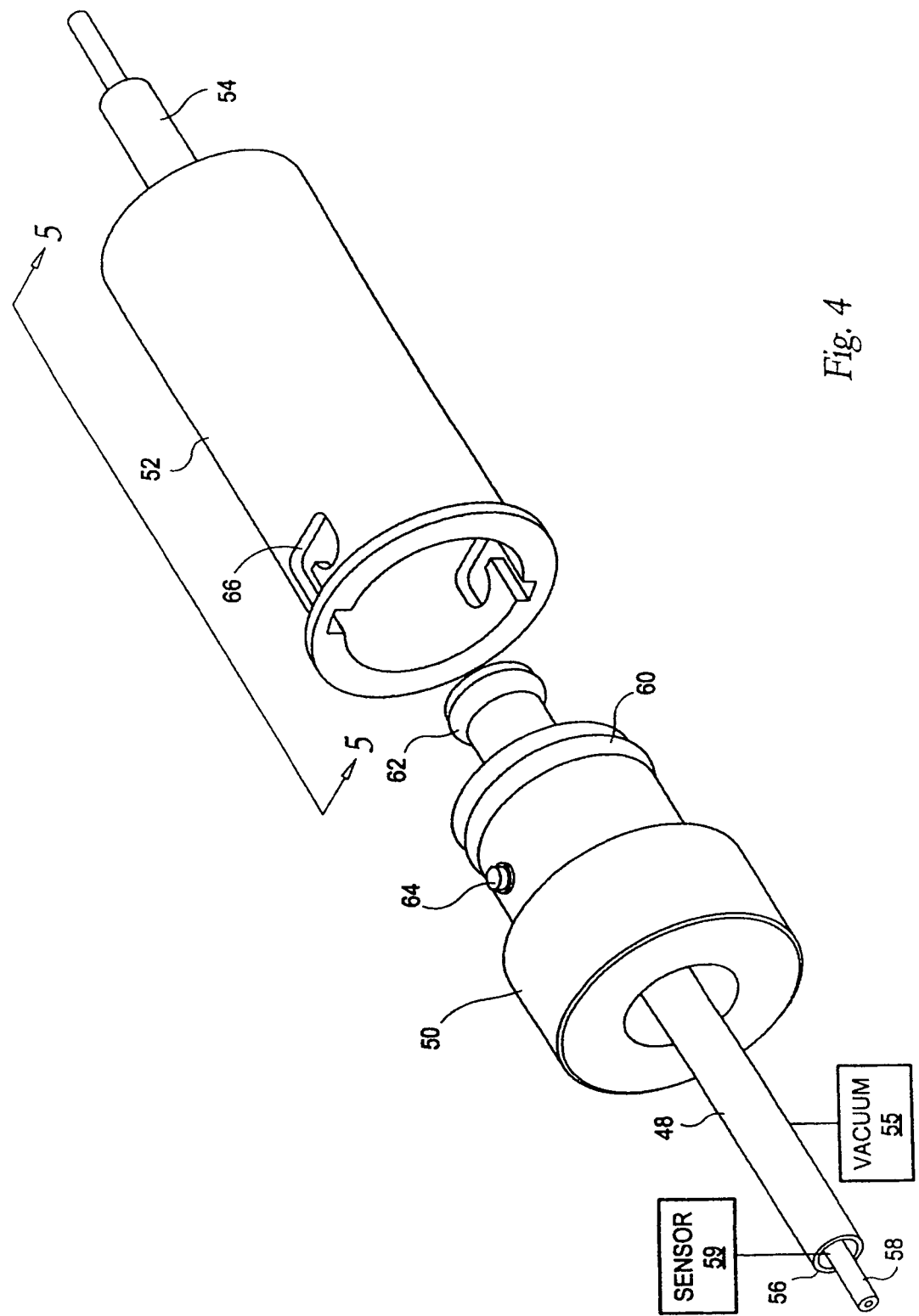
FIG. 4 is an exploded view of a two-part co-axial connector.

In addition to the above features, the refrigerant injection and low pressure or vacuum return lines can be configured coaxially either in an umbilical 18, catheter body 10, or in the handle 12, as shown in FIG. 4. In this illustration an umbilical 48, a first connector 50, a second connector 52, and second umbilical 54 or catheter are shown. The umbilical 48 includes an outer tube 56 and an inner tube 58. In the exemplary embodiment, the inner tube 58 provides a path for fluid (e.g., refrigerant) under positive pressure, whereas the outer tube 56 provides a path for fluid under reduced or low pressure (e.g., in connection to a vacuum pump 55). Thus, if a leak should occur at some point along the inner tube 58 or its connections to other components, the low pressure environment allows the leak to be contained, thereby preventing refrigerant from escaping the umbilical 48. Additional safety is provided by a sensor 59 in communication with the low-pressure fluid path defined by the outer tube 56. The sensor 59 is tuned to detect a change in pressure within the outer tube 56, and when a change is detected, fluid flow into the system is turned off, as a change in pressure can be an indicator that a leak is present in the system.

Continuing to refer to FIG. 4, the umbilical 48 is mated to the first connector 50 and the umbilical 54 is mated to the second connector 52. The first connector 50 includes O-rings 60 and 62 and is matable with the second connecter 52, as shown in greater detail in the figures that follow, to provide a fluid-tight connection. The first connector 50 can be locked to the second connector 52 with the assistance of a bayonet-type connection having complimentary protuberances 64 and engagement slots 66.

FIG. 5 is a cross-sectional view of the coaxial connector of FIG. 4 along line 5-5. In this view, the first connector 50 is shown almost fully mated to the second connector 52. In this view the inner tube 58 is shown mated to an inner portion 68 of the first connector 50. The inner portion 68 defines a fluid path 69 leading to an outlet 70 that, when the first and second connectors 50 and 52 are mated, aligns with a fluid inlet 72 to an injection tube 74. The O-ring 62 ensures good sealing of the connection.

Similarly, the outer tube 56 is shown mated to an outer portion 76 of the first connector 50. The outer portion defines a fluid path 78 that is in fluid communication with a fluid path 80 defined by the second connector 52. The fluid path 80 leads to, and is in communication with, a fluid path 82 in the umbilical 54. The O-ring 60 ensures a good seal between the first and second connectors 50 and 52, respectively.

Figure 6:
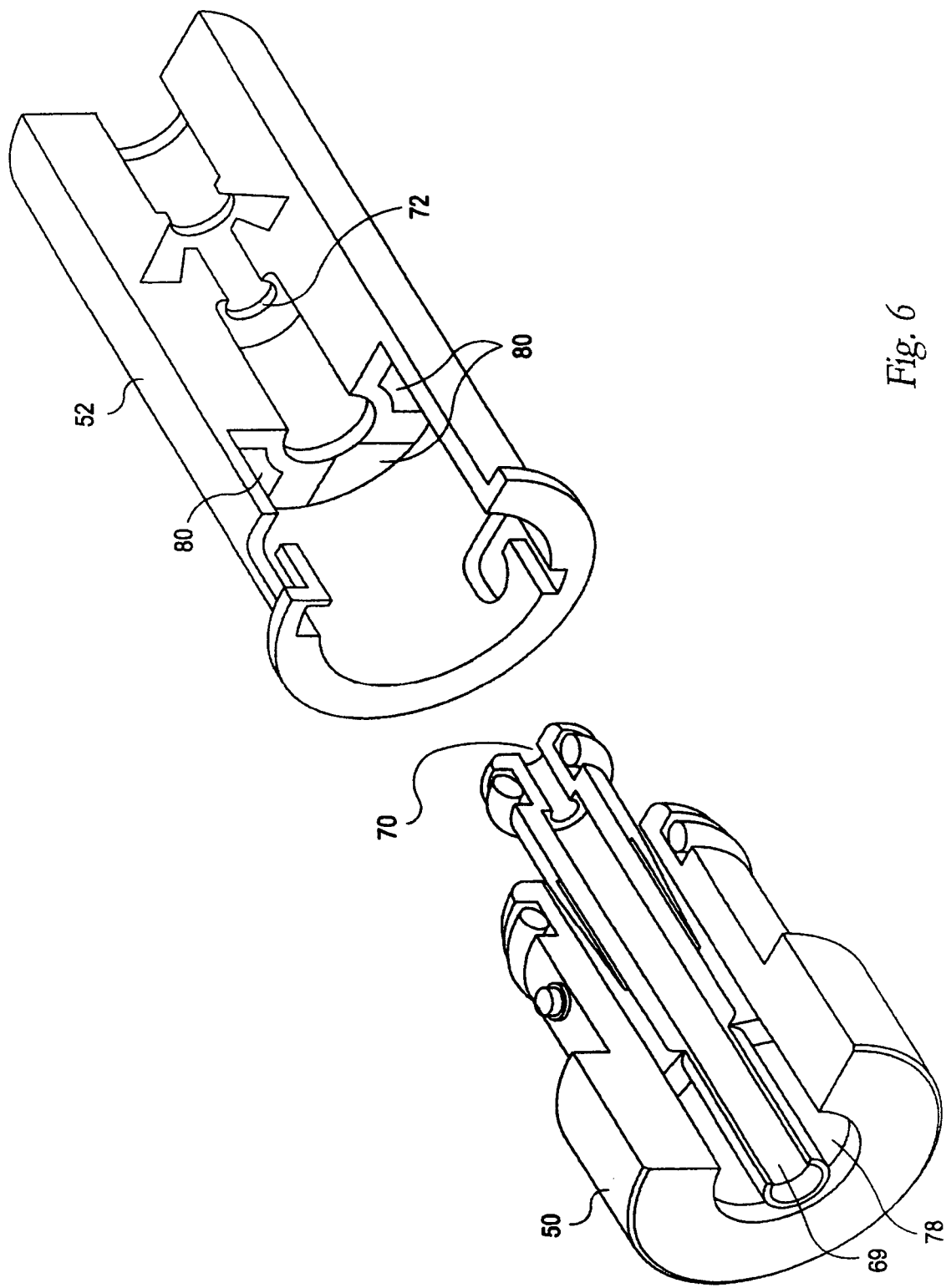
FIG. 6 illustrates additional features of the connector of FIG. 4 in an exploded cut-away view.

FIG. 6 is a cut-away view of the assembly shown in FIG. 4. In this view, the fluid path 69, outlet 70, fluid inlet 72, fluid path 78, fluid path 80 are all clearly visible.

FIG. 7 shows an alternative embodiment of a coaxial arrangement. Shown are a first connector 84 and a second connector 86. In this embodiment, a male Leur taper fitting 88 is receivable within a female Leur taper receptacle 90 as complimentary locking threads 92 and 94 on the first and second connectors are engaged. When the connectors are fully engaged an O-ring seal 96 prevents leakage for connecting fluid flow paths 98 and 100. Similarly, an o-ring seal 102 prevents leakage for connecting fluid flow paths 104 and 106. Exemplary fluid flow through flow paths 104 and 106 is shown by arrows.

Figure 8:
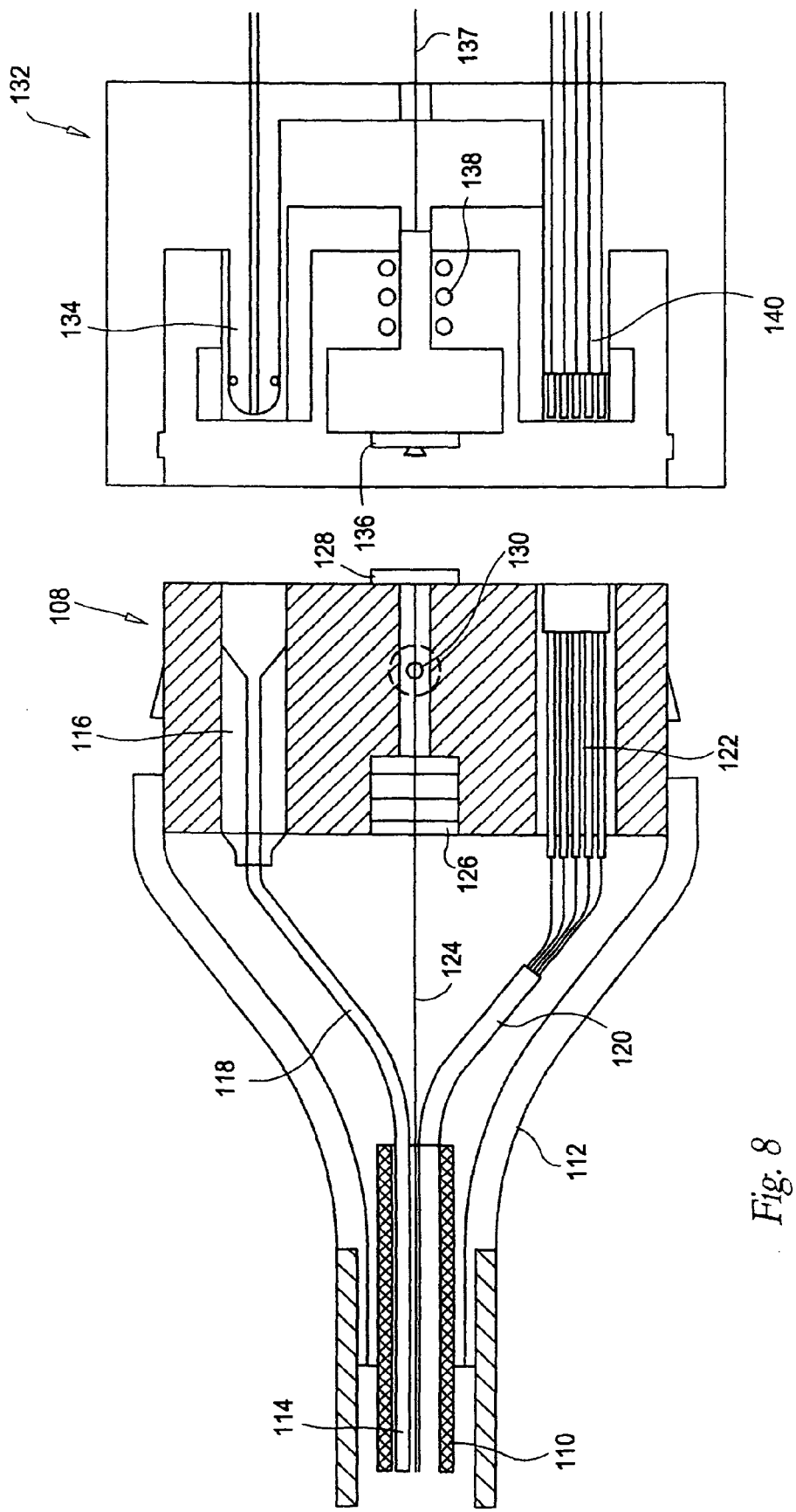
FIG. 8 is yet another embodiment of a co-axial connector.

Yet another connector embodiment is shown in FIG. 8. This embodiment provides connections that are not coaxial. As shown, a first connector 108 is mated to an outer tube or catheter shaft 110 with a rigid sleeve 112 and a flexible strain relief element. A fluid injection tube 114 is connected to a high-pressure female connector fitting 116 with a flexible connector tube 118. Electrical wires 120 that pass through the outer tube 110 terminate at a female pin wire connector 122. A pull-wire 124 passes through the outer tube 110 and a pull-wire seal fitting 126 to a female pull-wire connector 128. A pull-wire tension adjuster 130 can also be provided.

A second connector 132 includes a male, high-pressure connector 134 that is matable with the fitting 116 to provide a continuous fluid path. A male pull-wire connector 136, matable with the connector 128, is axially movable within a portion of the second connector 132 as shown by the double-headed arrow. The connector 136 is secured to a pull-wire 137 that is in turn secured to an actuator (such as element 36 shown in FIGS. 2 and 3). Thus, when the pull-wire 137 is moved axially, the connector 136 moves axially. A bias force can be applied by a bias element 138, such as a spring, to push the connector 136 to a selected point when axial tension is reduced on the pull-wire. Also shown is a male wire pin connector 140.

The present invention therefore provides for a number of fluid flow channels, tubes, or lumens to run through a two part detachable connector. The flow lumens generally consist of at least two lumens: one injection lumen, usually a conduit for high-pressure fluid flow, and one containment or return lumen, usually conduit for lower pressure fluid flow. Generally, the injection lumen allows for fluid to flow from the source to the tip of the catheter 10, while the return lumen allows for fluid flow to flow back from the tip of the catheter 10 to the console or recovery unit 22. As used herein, the term "lumen" shall mean any channel, conduit, or other enclosed space through which a fluid may flow, and may be defined by a single unitary element such as a tube or duct, or may be defined by a multitude of elements and surfaces.

The injection and return lumens may be arranged co-axially around a common primary axis, often being parallel to the axis of general fluid flow. Alternatively, the lumens may not be co-axially arranged, as in the connector of FIG. 8. However, the co-axial arrangement is advantageous in that when the return lumen surrounds the injection lumen, any leak from the injection lumen may be contained by the return lumen. Furthermore, the pressure in the return lumen may be lower than the ambient pressure outside the catheter, such as a negative gauge pressure, such that any rupture in the return lumen will not result in fluid escaping from the catheter. This greatly enhances the safety and efficacy of the catheter.

Figure 9A:
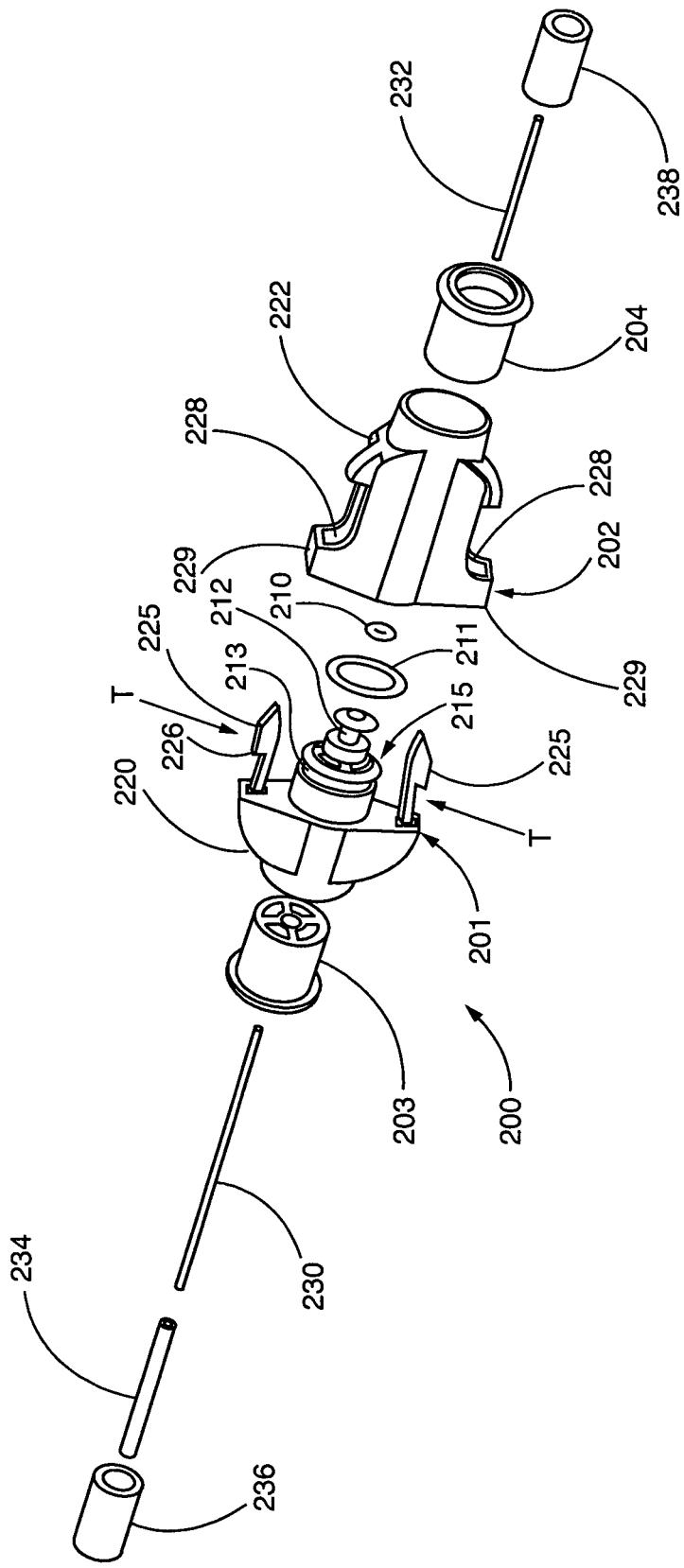
FIG. 9A is an exploded perspective view of yet another embodiment of a co-axial connector.

FIG. 9A is an exploded perspective view of one embodiment of a co-axial dual lumen connector, labeled generally as 200. Connector 200 includes a male coupling 201, a female coupling 202, and two plug fittings 203 and 204 for the male and female couplings 201 and 202, respectively. An inner O-ring 210 and an outer O-ring 211 are adapted to fit inside an inner circular groove 212 and an outer circular groove 213, respectively, on a shank 215 protruding from the body 220 of the male coupling 201, as shown.

The male coupling 201 further includes a mating mechanism, which includes two opposing locking prongs 225, with shoulders 226, protruding from the body 220, parallel to each other at opposite equidistant lateral positions spaced apart from the shank 215. The locking prongs 225 are adapted to be inserted into matching slots defined inside of opposing flanges 229 extruding from the body 222 of the female coupling 202, as shown. Each of the prongs 225 are flexible enough to be displaced inwards in the direction of arrows T towards the shank 215 such that the shoulder 226 abuts directly behind the flange 229 when the prong 225 is inserted through slot 228, thereby securing the male and female couplings 201 and 202 to each other.

A number of tubes and sleeves may be inserted into a number of channels or lumens (not shown) in both the male and female couplings 201 and 202. This includes a first injection tube 230, a second injection tube 232, co-axial injection sleeve 234, a first co-axial return tube 236 and a second co-axial return tube 238. The diameters of each tube are such that the co-axial injection sleeve is adapted to circumscribe the first injection tube 230 without leaving any space therebetween, while the first co-axial return tube is adapted to envelop the sleeve 234 so as to define a co-axial lumen therebetween, such lumen to form part of a return lumen throughout the connector. Sleeve 234 also protects the first injection tube 230 from kinking as well as insulating the fluid flowing therein.

FIG. 9B illustrates a side view of the assembled connector 200, showing the male coupling 201. The body 220 is shown having the plug fitting 203 inserted therein, as well as the injection tube 230 and sleeve 234. The plug 203 circumscribes an annular space 241 where the first co-axial return tube (not shown) is to be inserted. The plug also includes four spars 243 orthogonally disposed around an inner conduit 244. Inner conduit 244 of the plug 203 mates with another inner conduit (not shown) of disposed inside of the male coupling 201, such inner conduit of the male coupling circumscribing a portion of the injection tubing and sleeve 230 and 234. This annulus 241 further circumscribes the return lumen 245 defined between the inner surface of the annulus 241 and outer surface of sleeve 234. The injection tube 230 defines the injection lumen 250 which is centered directly co-incident which the central longitudinal axis (not shown) of the connector 200.

FIG. 9C illustrates a sectional view of the connector 200 taken along section X-X in FIG. 9B. In FIG. 9C, in addition to the elements shown and discussed in FIGS. 9A and 9B, the central longitudinal axis 255 is shown running through the injection lumen 250. The injection lumen itself includes a number of sections or lumens in fluid communication along the central longitudinal axis 255. This includes a central injection lumen 260 defined by the male plug fitting 203, followed by a central injection lumen 261 defined by the inner tube (not shown) disposed inside of the male coupling 201, followed by a central lumen 262 disposed at the tip of the shank 215 of the male coupling 201 and proximate the inner O-ring 210. This aggregation of longitudinal lumen sections disposed though the male coupling 201 is in fluid communication with an aggregation of longitudinal lumen sections disposed though the female coupling 202, including central lumen 263 defined by an inner conduit (not shown) in the female coupling 202, followed by a central lumen 264 defined by plug fitting 204. The return lumen is not shown in FIG. 9C due to the orientation of the spars, such as spars 243 through the plug 203, which run the length of the return lumen in each of the plug fittings 203 and 204, and the male and female couplings 201 and 202. Each set of spars is orthogonally disposed in general alignment with each other, such that section X-X runs directly through a plane coincident with a pair of diametrically opposed spars in each of the plug fittings 203 and 204, and the male and female couplings 201 and 202. FIG. 9C does not illustrate the first injection tube 230, second injection tube 232, co-axial injection sleeve 234, first co-axial return tube 236 and second co-axial return tube 238 inserted into connector 200.

Figure 9D:
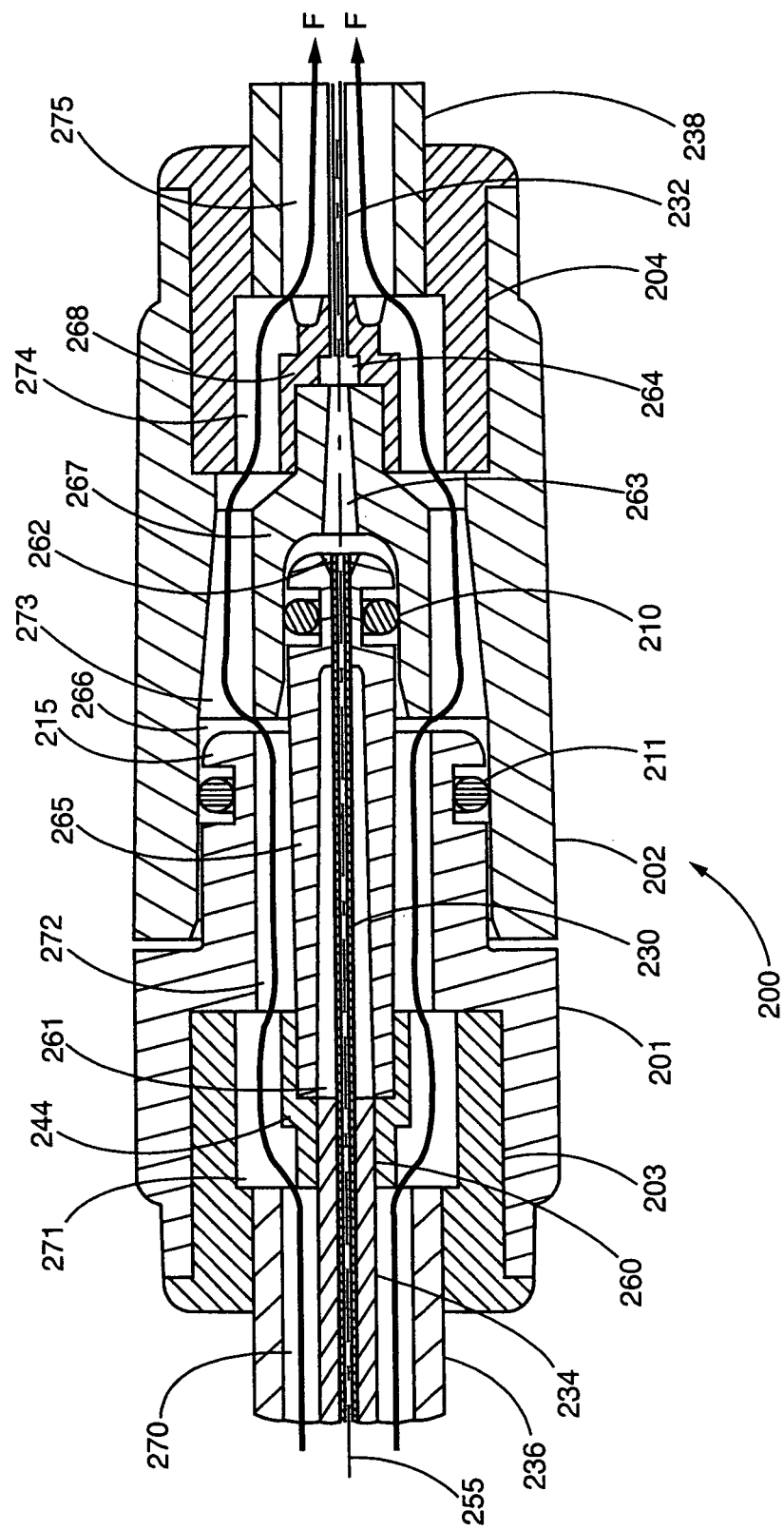
FIG. 9D is an enlarged sectional view of the connector of FIG. 9B taken along section W-W in FIG. 9B, with the injection and co-axial tubing inserted therein.

FIG. 9D is an enlarged alternate sectional view of the connector 200 taken along section W-W in FIG. 9B. In addition to the elements shown in FIG. 9C, FIG. 9D includes the first injection tube 230, second injection tube 232, co-axial injection sleeve 234, first co-axial return tube 236 and second co-axial return tube 238 inserted into connector 200. As shown in FIG. 9D, injection tube 230 is inserted co-axially around the central axis 255 into the central lumen 261 of the male coupling 201. Central lumen 261 is in turn defined by inner conduit 265, which is also co-axially centered around central axis 255. Sleeve 234 is disposed around a portion of injection tube 230 through central lumen 260 defined by inner conduit 244 of plug fitting 203, and extends outwardly from the connector 200 as shown. The sleeve 234 functions to anchor the injection tube 230 in place around the central axis 255 when the respective parts of the connector 200 are assembled and connected. Additionally, the first co-axial return tube 236 is shown inserted into plug 203, while the second co-axial return tube 238 is shown inserted into the plug 204.

The injection tube 230 runs straight through the length of shank 215 of the male coupling 201 and through the central lumen 262 defined by the tip portion of said shank 215. The distal end of the injection tube 230 is therefore in direct fluid communication with the central lumen 263 of the female coupling 202, defined by inner conduit 267. As shown in FIG. 9D, central lumen 264 is in fluid communication with central lumen 264 defined by inner conduit 268 of plug 204 inserted into the female coupling 202. A second injection tube 232 is in turn inserted into a portion of the central lumen 264 and is in fluid communication therewith. Thus fluid entering or leaving through the proximal end of injection tube 230 will flow through the tube 230, through male coupling 201, into female coupling 202 and through injection tube 232, always centered around central axis 255. Generally the flow of fluid through such a fluid pathway is suitable for high pressure, pure or mixed phase refrigerants, gases, or liquids, adapted for cryogenic expansion and evaporation at the catheter tip so as to trigger cryoablation. The fluid is hence "injected" to the tip of the catheter through such an injection pathway. It will be appreciated that the injection of such fluid may be in either direction, whether from the male coupling 201 to the female coupling 202, or from the female coupling 202 to the male coupling 201, depending on the particular orientation of the connector 200 in the catheter system.

In addition to flow of injection fluid through a first fluid flow pathway along a central longitudinal axis, the connector 200 provides a second fluid flow pathway, disposed co-axially about the first fluid flow pathway and central longitudinal axis, as more fully described below. Such a second flow pathway or channel is advantageous in several ways. First, it provides a means by which the fluid injected to the catheter tip may be recovered by the catheter system in a closed loop flow configuration. For this function, such a pathway, which runs through a significant length of the catheter and catheter system, may be referred to as a "return" lumen. Second, it provides a means whereby the flow of fluid throughout the catheter may be contained so as to prevent leaks. For both functions, the return lumen is generally at a pressure lower than that of the pressure along the first fluid pathway, and often lower than the ambient pressure found outside the catheter itself. Such lower pressures may at times be below zero gauge pressure so as to render the return lumen a "vacuum return lumen."

As shown in FIG. 9D, the second fluid flow pathway through connector 200 (being the portion of the return lumen of the catheter system which runs through the connector 200) is defined by several sections of lumen disposed co-axially around the central axis 255. If the flow of fluid were to flow along the path traced arrows F shown in FIG. 9D, the return lumen would commence with co-axial lumen 270 defined by the annular space between the first co-axial return tube 236 and sleeve 234. Co-axial lumen 270 is in fluid communication with co-axial lumen 271 defined by the annular space between the outer rim of plug 203 and its inner conduit 244. The second fluid pathway continues with co-axial lumen 272 defined by the annular space enveloping inner conduit 265 of male coupling 201. The second fluid pathway thereafter exits the distal end of male coupling 201 through shank 215 and enters the narrow annular disk of space 266 defined by the mating of male coupling 201 and female coupling 202. Outer O-ring 211 prevents the escape of fluid from space 266 out of connector 200.

The second flow pathway continues with co-axial lumen 273 that is in fluid communication with space 266 and is defined by an annular space enveloping inner conduit 267 of female coupling 202. Lumen 273 is in fluid communication with co-axial lumen 274 defined by the annular space between the outer rim of plug 204 and its inner conduit 268. Lumen 274 is in fluid communication with annular lumen 275 defined by the second co-axial return tube 238 and second injection tube 232.

Thus the flow of fluid runs through the second pathway along direction F as shown. Of course, the fluid flow may be reversed and runs opposite to the direction F as shown. However, the flow of fluid in the second pathway is generally opposite in direction to the flow of fluid through the first pathway or injection lumen. For cryoablation, representative fluid pressures range from 400 to 800 psia in the first, injection flow pathway and 0 to 20 psia in the second, return flow pathway.

FIG. 10A is an exploded perspective view of another catheter connector in accordance with the principles of the present invention, labeled generally as 300. Connector 300 is another embodiment of a co-axial, dual flow pathway connector. Connector 300 is suitable for use with high-pressure catheter systems and shares many of the same internal flow lumen, conduit, and fluid channel configurations as connector 200.

Turning now to FIG. 10A, connector 300 includes a female coupling member 301, a male coupling member 302, a female co-axial plug member 303, and a male co-axial plug member 304. All of the components of connector 300 are co-axially centered on a central longitudinal axis 305 as shown. Male coupling 302 includes a shank 310 very similar to that of shank 215 of male coupling 201 of connector 200. For its mating mechanism, shank 310 includes two diametrically opposed protuberances 312 adapted to slide into diametrically opposed arcuate grooves 315 disposed into the mating end 316 of female coupling 301. As used herein, a "protuberance" shall mean any structural element extending from a body or surface, such as a flange, beam, finger, or other extrusion. In this case, protuberances 312 are cylindrically shaped beams jutting out from opposing lateral sides of shank 310. Shank 310 also includes two O-rings (not shown) adapted to fit into circumferential grooves 317 and 318, much like the O-rings of connector 200.

As illustrated in FIG. 10A, the orientation of the protuberances 312 are such that when male coupling 302 is rotated 180 degrees about central axis 305 its geometric orientation does not change. For example, for every rotation of 180 degrees about axis 305, the protuberances 312 are positioned the same with respect to a fixed point in space. The same rotational symmetry applies to female coupling 301. When female coupling 302 is rotated 180 degrees about central axis 305 its geometric orientation does not change: the arcuate grooves 315 are positioned the same with respect to a fixed point in space. As shown in FIG. 10A, arcuate grooves 315 are J-shaped and span an arc of about ninety degrees.

The male and female couplings of connector 300 are connected when the male coupling 302 is inserted into the female coupling 301 such that protuberances 312 slide into the mating end 316 of grooves 315 and by rotating the male coupling 302 relative to the female coupling 301 by about 45 degrees in the direction C as shown. The assembled connector is shown in FIG. 10B. Each of grooves 315 includes a semi-circular locking enclosure 320 at its distal end, shaped to conform tightly to the outline of protuberance 312 so as to frictionally grip the protuberance 312 in place and thereby hold couplings 301 and 302 together.

FIG. 10C shows the connector of FIG. 10B on a plane to which axis 305 is a normal axis, illustrating the orientation of protuberances 312. As shown in FIG. 10C, protuberances 312 jut out non-perpendicular to the surface of shank 310, so as to fit into grooves 315 when inserted therein in a rotating path.

Connector 300 has certain advantages over previous known catheter connectors of this type, and indeed over the connector 200 previously discussed herein. Because male coupling 302 can only be inserted into female coupling 301 by inserting the protuberances 312 into grooves 301, the co-axial connection of first and second fluid pathways therein is made only by properly locking the couplings into place. This may not have been the case with connector 200 for example. It will be appreciated, by careful examination of the orientation of components of connector 200 in FIG. 9A, that shank 215 could potentially be inserted into female coupling 202 without having to inserted prongs 225 though slots 228. All the internal fluid pathways would still be linked, due to the co-axial geometry of such flow pathways, but the locking mechanism of connector 200 would not be properly engaged. Connector 300 however, solves this problem by allowing the couplings 301 and 302 to be coupled only by simultaneous engagement of the locking mechanism.

FIG. 11A is an exploded perspective view of yet another embodiment of a co-axial dual lumen catheter connector, labeled generally as 400. Connector 400 is similar to connectors 200 and 300 in that it shares the same internal dual co-axial flow pathway arrangement. Connector 400 is also similar to connector 300 in that it shares a locking mechanism that must be simultaneously engaged as the couplings of the connector are mated.

Connector 400 includes a female coupling 401 and a male coupling 402, each with respective mating ends 403 and 404. Both of couplings 401 and 402 are co-axially centered on a central longitudinal axis 405 as shown. Male coupling 402 includes a shank 410 jutting out from its mating end 404, very similar to the shanks of connectors 200 and 300. For its mating mechanism, male coupling 402 also includes two diametrically opposed L-shaped locking prongs 415 circumferentially disposed about shank 410, and jutting out from mating end 404 as shown. Female coupling 401 includes a pair of diametrically opposed L-shaped enclosures or cavities 417, partially defined by a pair of diametrically opposed extrusions 418 spacedly disposed apart from an outer rim 420 enclosing the recess 422 for receiving shank 410. As used herein, an "enclosure" shall mean any space or void of a particular shape adapted to receive a structural element of similar shape and dimension, and as defined by various structural elements adjacent thereto, such as, a groove, a slot, a cavity, or a hollow. Each locking prong 415 is separated from shank 410 by an annular sector (not clearly shown) into which the outer rim 420 slides when the two couplings are engaged as shown in FIG. 11B.

FIG. 11C illustrates a view of the mating end 404 of male coupling 402. As shown, the prongs 415 are radially spaced apart from shank 410 by annular sectors or grooves 425, which tightly receive outer rim 420 of female coupling 401. Turning back to FIG. 11A, male coupling 402 is inserted into female coupling 401 by aligning the prongs 415 to be positioned just laterally of extrusions 418. The shank 410 is thereafter inserted into recess 422 while male coupling is rotated relative to the female coupling about axis 405 in the direction C as shown. Connector 400 therefore functions in much the same way as connector 300, except that the frictional contact surface area between L-shaped prongs 415 and their complementary L-shaped enclosures 417 is much higher than that of the protuberances 312 and locking enclosures 320 of connector 300, thereby allowing for greater control of the locking force and overall coupling action of the connector.

FIG. 12A is an exploded perspective view of yet another embodiment of a co-axial dual lumen catheter connector, labeled generally as 500. Connector 500 is similar to connectors 200, 300 and 400 in that it shares the same internal dual co-axial flow pathway arrangement. Connector 500 is also similar to connector 300 and 400 in that it shares a locking mechanism that must be simultaneously engaged as the couplings of the connector are mated.

Connector 500 includes a male coupling 501 and a female coupling 502, each of which are co-axially centered on a central longitudinal axis 503 as shown. Male coupling 501 includes a shank 505 very similar to the shanks 215, 310, and 410 of connectors 200, 300, and 400 respectively. However, shank 505 also includes a pair of diametrically opposed spiral ledges 515 that each run 180 degrees about the base 516 of shank 505 as shown. Each ledge 516 commences at the base 516 of the shank 505 and spirals around the shank 505 for 180 degrees about axis 503, and spirals a longitudinal distance along central axis 503 as shown, to end just short of the outer O-ring (not shown) circumferential groove 517. Another ledge 515 is disposed about the other 180 degrees of the base 516 of shank 505, sloping away from the base 516 at its starting point 519, in the direction C about axis 503.

Male coupling 501 also includes two diametrically opposed locking prongs 510 spaced apart from shank 505. Female coupling 502 also includes a pair of diametrically opposed hooks 520. When male coupling 501 is inserted into female coupling 502, each locking prong 510 is adapted to be partially enclosed by its complementary hook 520.

However, male coupling 501 is not insertable into female coupling 502 simply by inserting the prongs directly into hooks 520 in the direction of arrows A as shown in FIG. 12A. As illustrated in FIG. 12B, the inner surface 522 of recess 523 of female coupling 502 includes two diametrically opposed spiral ledges 525. Each ledge 525 is complementary to a ledge 515 of the male coupling 501, such that when the two couplings are fully mated, the entirety of each of ledge 525 is in contact with the entirety of each of ledge 525. Female coupling 502 is thus mated to male coupling 501 by first rotating the female coupling 502 relative to male coupling 501 about axis 503 in the direction C shown in FIG. 12A such that each hook 520 is radially displaced away from prong 510. The two couplings are thereafter mated together by rotatably (in the direction opposite to C about axis 503) inserting the shank 505 into recess 523 such that the ledges 515 and 525 come into contact and slide relative to each other until the endpoint 527 of ledge 525 is proximate the starting point 519 of ledge 515. FIG. 12C shows the two couplings 501 and 502 in mated form.

FIG. 13A is an exploded perspective view of another embodiment of a co-axial dual lumen connector, labeled generally as 600. Connector 600 includes a male coupling 601, a female coupling 602, and two plug fittings 603 and 604 for the male and female couplings 601 and 602, respectively. An inner O-ring 610 and an outer O-ring 611 are adapted to fit inside an inner circular groove 612 and an outer circular groove 613, respectively, on a shank 615 protruding from the body 620 of the male coupling 601, as shown.

The male coupling 601 further includes two opposing locking prongs 625, with shoulders 626, protruding from the body 620, parallel to each other at opposite equidistant lateral positions spaced apart from the shank 615. The locking prongs 625 are adapted to be inserted through any one of six enclosures 627 defined by outer ring 628 and any two adjacent spars 629 connecting outer ring 628 to the body 622 of female coupling 602, as shown. Each of the prongs 625 are flexible enough to be displaced inwards in the direction of arrows T towards the shank 615 such that the shoulder 626 abuts directly behind the outer ring 628 when the prong 625 is inserted through enclosure 627, thereby securing the male and female couplings 601 and 602 to each other.

A number of tubes and sleeves may be inserted into a number of channels or lumens (not shown) in both the male and female couplings 601 and 602. This includes a first injection tube 630, a second injection tube 632, co-axial injection sleeve 634, a first co-axial return tube 636 and a second co-axial return tube 638. The diameters of each tube are such that the co-axial injection sleeve 634 is adapted to circumscribe the first injection tube 630 without leaving any space therebetween, while the first co-axial return tube 636 is adapted to envelop the sleeve 634 so as to define a co-axial lumen therebetween, such lumen to form part of a return lumen throughout the connector, similar to the arrangement of components of connector 200.

FIG. 13B illustrates connector 600 in mated form taken along a longitudinal section coincident with central axis 640 of FIG. 13A. Both the injection fluid flow pathway, coincident with central axis 640, and the co-axial return flow pathway co-incident with arrows F as shown. Thus the internal flow lumen arrangement of connector 600 is very similar to that of connector 200. In addition, a ridge 645 is shown extruding from outer ring 628. Ridge 645 runs around the entire circumference of outer ring 628, and is disposed such that when prong 625 is inserted into female coupling 602, the shoulder 626 of prong 625 abuts against the ridge 645, locking the male coupling 601 with female coupling 602.

FIG. 14A is an exploded perspective view of one embodiment of a double co-axial or "tri-axial" connector, labeled generally as 700. Connector 700 includes a male coupling 701, a female coupling 702, and two plug fittings 703 and 704 for the male and female couplings 701 and 702, respectively. An inner O-ring 709, an intermediate O-ring 710, and an outer O-ring 711 are adapted to fit inside an inner circular grooves 712, 713, and 714, respectively, on a shank 715 protruding from the body 720 of the male coupling 701, as shown.

The male coupling 701 further includes two opposing locking prongs 725, with shoulders 726, protruding from the body 720, parallel to each other at opposite equidistant lateral positions spaced apart from the shank 715. The locking prongs 725 are adapted to be inserted U-shaped slot enclosures 727 defined by outer ring 728 of female coupling 702, as shown. Each of the prongs 725 are flexible enough to be displaced inwards in the direction of arrows T towards the shank 715 such that the shoulder 726 abuts directly behind a respective U-shaped slot enclosures 727 when prong 725 is inserted therein, thereby securing the male and female couplings 701 and 702 to each other.

A number of tubes and sleeves may be inserted into a number of channels or lumens (not shown) in both the male and female couplings 701 and 702. This includes a first injection tube 730, a second injection tube 732, a first co-axial injection sleeve 734, a second co-axial injection sleeve 735, a first co-axial return tube 736 and a second co-axial return tube 738. Within the male coupling 701, the diameters of the tubes are such that the first co-axial injection sleeve 734 is adapted to circumscribe the first injection tube 730 without leaving any space therebetween, while the first co-axial return tube 736 is adapted to envelop the sleeve 734 so as to define a co-axial lumen therebetween, such lumen to form part of a return lumen throughout the connector, similar to the arrangement of components of connectors 200 and 600. The second injection tube 732, second co-axial injection sleeve 735, and second co-axial return tube 738 are similarly arranged through the female coupling 702, thereby creating first and second fluid flow pathways through the connector 700 when the male and female couplings 710 and 702 are mated. FIG. 14B illustrated the connector 700 in partially mated form, with each of male coupling 701 and female coupling 702 having its respective injection and co-axial tubing inserted. FIG. 14C shows the connector 700 in fully mated form.

In addition to one co-axial lumen surrounding a central flow injection lumen, connector 700 provides a second lumen in addition to the first lumen, such that connector 700 provides first, second, and third fluid flow pathways. The second lumen may be co-axial around the first and second fluid flow pathways, or it may simply be separate and distinct from the first lumen, and may be incorporated in the first return tube 736 and second return tube 738. The outermost co-axial lumen may therefore serve as a "double vacuum" lumen, providing yet another layer of safety and vacuum operation to the catheter system.

FIG. 14D is a side view of the connector of FIG. 14A in fully assembled form, showing the female coupling 702. FIG. 14E is a sectional view of the connector of FIG. 14A taken along section A-A in FIG. 14D, while FIG. 14F is a sectional view of the connector of FIG. 14A taken along section Z-Z in FIG. 14D. In addition to the elements shown in FIG. 14A, the first fluid pathway, or injection lumen 740, second fluid pathway, or first return lumen 745, and third fluid pathway, or second return lumen 750, are shown.

Figure 15A:
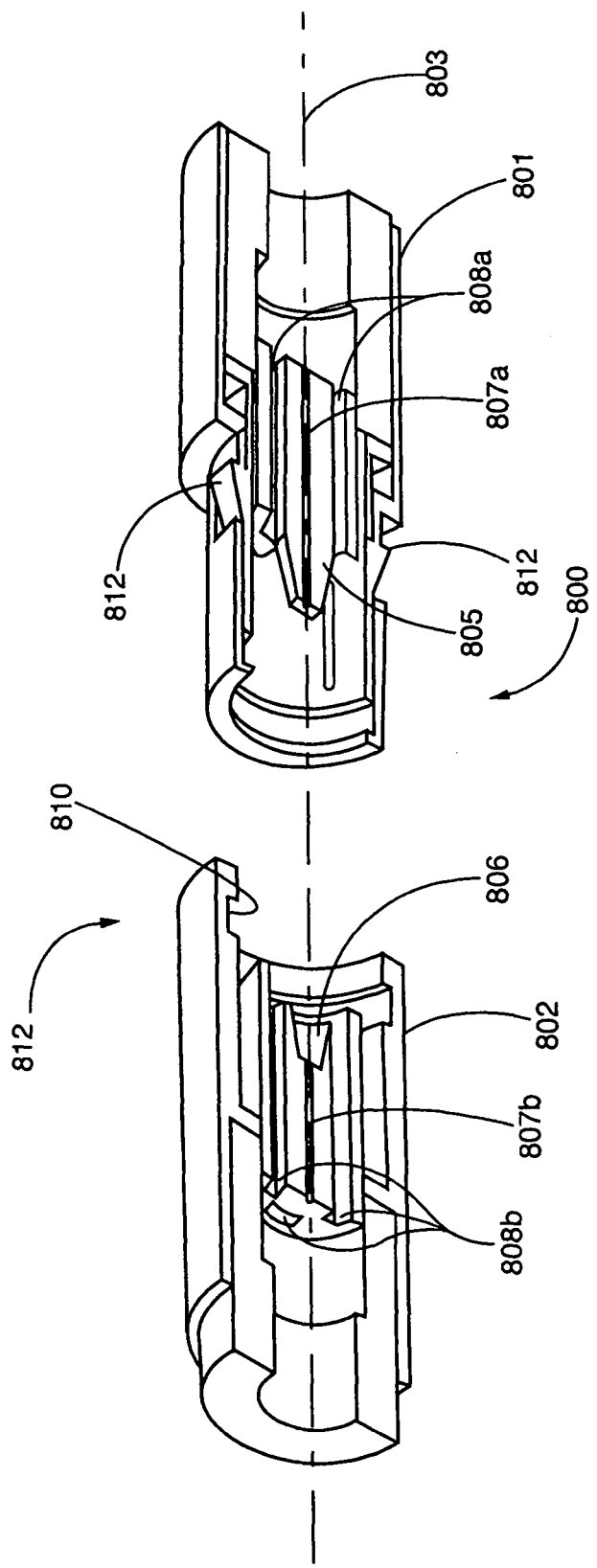
FIG. 15A is a cutaway, exploded perspective view of yet another embodiment of a co-axial connector.

FIG. 15A is a cutaway, exploded perspective view of yet another embodiment of a co-axial connector of the present invention, labeled generally as 800. Connector 800 includes a male coupling 801 and a female coupling 802, each of which are co-axially centered on a central longitudinal axis 803 as shown. Male coupling 801 includes a tapered central shank 805 which fits into a complementary tapered female recess 806 in female coupling 802. Each male and female coupling further includes a central injection lumen 807a and 807b, respectively, centered about central longitudinal axis 803 as shown. Each male and female coupling further includes a plurality of co-axial lumens 808a and 808b, respectively, centered about central longitudinal axis 803, and about the injection lumens 807a and 807b, as shown.

Female coupling 802 includes a circumferential slot 810, being an annular recess disposed within the mating end 812 of the female coupling 802. Male coupling 801 includes a pair of diametrically opposed locking prongs 812 included outside of the inner lumens that are disposed to slide into the circumferential slot 810.

FIG. 15B is an enlarged cutaway, exploded perspective view of the connector of FIG. 15A in mated form. As illustrated in FIG. 15B, central injection lumens 807a and 807b mate to form a contiguous central lumen, which acts as a first pathway for fluid flow. Furthermore, outer co-axial lumens 808a and 808b merge to form several outer co-axial pathways for fluid flow, of which only a portion are shown, due to the cutaway view. The locking prongs 812 are shown engaged into the slot 810, thereby fastening and mating the two couplings 801 and 802 together.

Figure 15C:
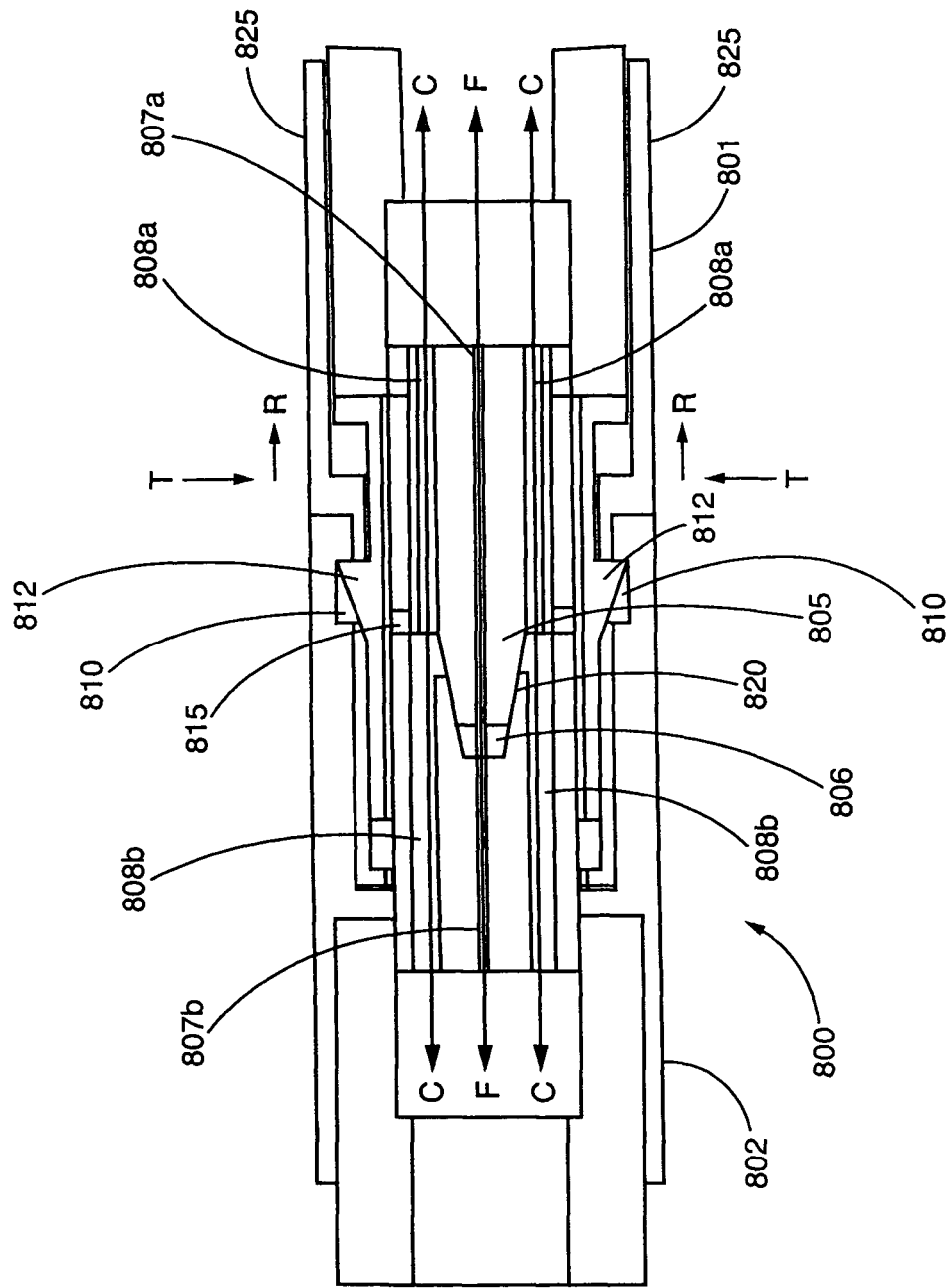
FIG. 15C is a cross-sectional view of the connector of FIG. 15A in mated form.

FIG. 15C is a cross-sectional view of the connector of FIG. 15A in mated form. As shown in FIG. 15C, the first fluid pathway is defined by arrows F, wherein fluid is free to move in either direction along pathway F along the central lumen formed by the merging of lumens 807a and 807b. A second fluid pathway is defined by the plurality of outer co-axial lumens 808a and 808b along the direction of arrows C. Once again, fluid is passable in either direction.

Connector 800 further includes an O-ring 815 to seal the inner lumens from the outside environment. The interface 820 between the male tapered shank 805 and the female recess 806 is sealed by the shear action between the respective surfaces when couplings 801 and 802 are mated. This sealing along interface 820 isolated the central injection lumen from the outer co-axial lumens.

To release male coupling 801 from female coupling 802, an outer sliding sleeve 825 is circumferentially disposed about the male coupling 801. The sleeve 825 slides in the direction R as shown, which in turn forces prongs 812 to deflect inwards in the direction of arrows T as shown, thereby translating free of slot 810 to decouple the couplings.

Any of the above described connectors can be connected to an umbilical having a first portion and a second portion, and/or to a catheter or other medical device. These connectors provide connecting structure for the various umbilicals as well as for the various medical devices discussed in this and the incorporated patent applications.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A thermal treatment medical system, comprising:
   an umbilical having a first portion sized to receive a second portion, wherein the second portion is a medical catheter; and
   a connector including
      a first coupling member connected to the first portion and including a protuberance, the first coupling member having a first central longitudinal axis and a first electrical connector,
      a second coupling member connected to the second portion, the second coupling member defining a slot on its outer surface sized to receive the protuberance and a second electrical connector matable with the first electrical connector, the second coupling member having a second central longitudinal axis coincident with the first central longitudinal axis, the second coupling member being insertable into the first coupling member to define first, second, and third fluid flow pathways, the first fluid flow pathway being coincident with the first central longitudinal axis, the second fluid flow pathway being co-axially disposed around the first fluid flow pathway, the third fluid flow pathway being co-axially disposed about the central longitudinal axis, the third fluid flow pathway being circumferentially disposed about the second fluid flow pathway;
   a pressure sensor coupled to the umbilical and in fluid communication with at least one of the first and second fluid pathways; and
   a means for releasably securing the coupling of the first and second coupling members.

2. The thermal treatment medical system of claim 1, wherein the means for coupling the first and second coupling members includes a means for inserting the first coupling member into the second coupling member through translation of the first coupling member relative to the second coupling member longitudinally along said central longitudinal axis, and simultaneous rotation of the first coupling member relative to the second coupling member about said central longitudinal axis.

3. The thermal treatment medical system of claim 1, wherein the first portion of the umbilical is connected to a surgical instrument.

4. The thermal treatment medical system of claim 3, wherein the second portion of the umbilical is connected to a console for operating the surgical instrument.

\* \* \* \* \*